United States Patent
Chung et al.

(10) Patent No.: US 10,576,044 B2
(45) Date of Patent: Mar. 3, 2020

(54) COENZYME Q10 SOLUBILIZING COMPOSITION AND METHOD FOR PREPARING SAME

(71) Applicant: ABTIS CO., LTD., Gyeonggi-do (KR)

(72) Inventors: Sang Jeon Chung, Seoul (KR); Ju Hwan Kim, Seoul (KR); Hyo Jin Kang, Seoul (KR)

(73) Assignee: ABTIS CO., LTD. (KR)

( * ) Notice: Subject to any disclaimer, the term of this patent is extended or adjusted under 35 U.S.C. 154(b) by 0 days.

(21) Appl. No.: 16/094,042

(22) PCT Filed: Apr. 19, 2017

(86) PCT No.: PCT/KR2017/004182
§ 371 (c)(1),
(2) Date: Oct. 16, 2018

(87) PCT Pub. No.: WO2017/183901
PCT Pub. Date: Oct. 26, 2017

(65) Prior Publication Data
US 2019/0133969 A1    May 9, 2019

(30) Foreign Application Priority Data

Apr. 19, 2016 (KR) .................. 10-2016-0047838
Apr. 18, 2017 (KR) .................. 10-2017-0049881

(51) Int. Cl.
*A61K 31/122* (2006.01)
*A61K 8/63* (2006.01)
(Continued)

(52) U.S. Cl.
CPC .............. *A61K 31/122* (2013.01); *A61K 8/14* (2013.01); *A61K 8/347* (2013.01); *A61K 8/35* (2013.01);
(Continued)

(58) Field of Classification Search
CPC .............. A61K 2300/00; A61K 31/122; A61K 31/375; A61K 2800/10; A61K 31/12;
(Continued)

(56) References Cited

FOREIGN PATENT DOCUMENTS

JP        2002505307 A    2/2002
JP    WO2013180253 A1    1/2016
(Continued)

OTHER PUBLICATIONS

Translation of the amendment filed for KR 1020050004945.*
(Continued)

*Primary Examiner* — Savitha M Rao
(74) *Attorney, Agent, or Firm* — Riverside Law LLP

(57) ABSTRACT

The present invention relates to a coenzyme Q10 solubilizing composition and a method for preparing the same. In the coenzyme Q10 solubilizing composition and the method for preparing the same according to the present invention, coenzyme Q10, which is a non-soluble drug, is encapsulated by a micelle containing glycyrrhizic acid or a salt of glycyrrhizic acid, bile acid, and unsaturated fatty acid, thereby improving encapsulation efficiency and improving the solubility of coenzyme Q10 in water. In addition, the mass-production of the composition can be easily achieved through sonication or a microfluidizer, the particle size of the composition encapsulating coenzyme Q10 can be controlled, and the natural substance-based formulation without using ethanol and an organic solvent are possible, so that it is expected that the composition of the present invention can be favorably utilized as a composition for pharmaceuticals, foods, and cosmetics, the composition having ensured stability and almost no toxicity.

14 Claims, 21 Drawing Sheets

(51) Int. Cl.
  *A61K 47/14* (2017.01)
  *A61K 47/26* (2006.01)
  *A61K 47/28* (2006.01)
  *A61K 31/575* (2006.01)
  *A61K 31/704* (2006.01)
  *A61K 8/14* (2006.01)
  *A61K 47/22* (2006.01)
  *A61K 8/67* (2006.01)
  *A61Q 19/00* (2006.01)
  *A61K 9/107* (2006.01)
  *A61K 8/36* (2006.01)
  *A61K 8/34* (2006.01)
  *A61K 8/35* (2006.01)
  *A61K 8/60* (2006.01)
  *A61K 9/19* (2006.01)

(52) U.S. Cl.
  CPC ............... *A61K 8/361* (2013.01); *A61K 8/60* (2013.01); *A61K 8/63* (2013.01); *A61K 8/676* (2013.01); *A61K 9/107* (2013.01); *A61K 9/1075* (2013.01); *A61K 31/575* (2013.01); *A61K 31/704* (2013.01); *A61K 47/14* (2013.01); *A61K 47/22* (2013.01); *A61K 47/26* (2013.01); *A61K 47/28* (2013.01); *A61Q 19/00* (2013.01); *A61K 9/19* (2013.01); *A61K 2800/10* (2013.01)

(58) Field of Classification Search
  CPC .. A61K 31/337; A61K 31/575; A61K 31/704; A61K 47/14; A61K 47/22; A61K 47/26; A61K 47/28; A61K 8/14; A61K 8/347; A61K 8/35; A61K 8/361; A61K 8/60; A61K 8/63; A61K 8/676; A61K 9/107; A61K 9/1075; A61K 9/19; A23L 33/10; A61Q 19/00

See application file for complete search history.

(56) References Cited

FOREIGN PATENT DOCUMENTS

| KR | 1020050004945 A | 1/2005 |
| KR | 1020080015070 A | 2/2008 |
| KR | 100871050 B1 | 12/2008 |
| KR | 1020100131391 A | 12/2010 |
| KR | 1020110089125 A | 8/2011 |
| KR | 1020140043574 A | 4/2014 |

OTHER PUBLICATIONS

Polyakov et al. (The open conference proceedings journal, 2011, vol. 2, pp. 64-72).*

Goncalves et al., "Micellar lipid composition affects micelle interaction with class B scavenger receptor extracellular loops," J. Lipid Res., 2015, 56:1123-1133.

Uekaji et al., "A New Generation of Nutra-ceuticals and Cosme-ceuticals Complexing lipophilic bioactives with γ-cyclodextrin," Transactions of the Materials Research Society of Japan, 2012, 37(1):89-94.

Pinsolle et al., "Colloids and Surfaces B: Biointerfaces," Colloids and Surfaces B: Biointerfaces, 2013, 106:191-197.

Uekaji et al., "Application of γ-Cyclodextrin in Nanomedicinal Foods and Cosmetics", Bio-Nanotechnology: A Revolution in Food, Biomedical and Health Sciences, First Edition, 2013, Chapter 10, pp. 179-211.

* cited by examiner

Supersaturated CoQ10 micelle preparation

FIG. 8

System

Temperature (°C): 25.0
Count Rate (kcps): 275.1
Cell Description: Clear disposable zeta c...

Zeta Runs: 20
Measurement Position (mm): 2.00
Attenuator: 11

Results

|  | Mean (mV) | Area (%) | St Dev (mV) |
|---|---|---|---|
| Peak 1: | 0.00 | 0.0 | 0.00 |
| Peak 2: | 0.00 | 0.0 | 0.00 |
| Peak 3: | 0.00 | 0.0 | 0.00 |

Zeta Potential (mV): -46.9
Zeta Deviation (mV): 0.00
Conductivity (mS/cm): 18.9
Result quality: Good

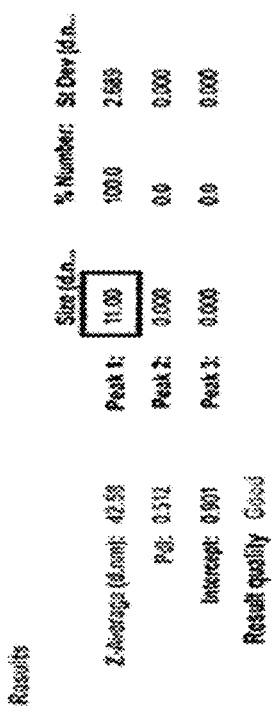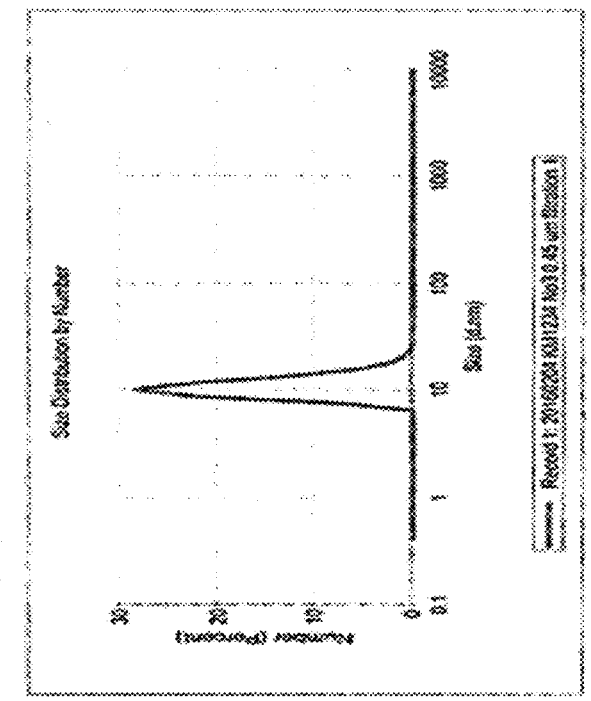
FIG. 10

COENZYME Q10 SOLUBILIZING COMPOSITION AND METHOD FOR PREPARING SAME

STATEMENT REGARDING GOVERNMENT RIGHTS

The present invention was undertaken with the support of Bio-Synergy Research Project (NRF-2012M3A9C4048775) grant funded by the Ministry of Science and ICT through NRF Korea.

CROSS-REFERENCE TO RELATED APPLICATIONS

This application claims priority to and the benefit of Korean Patent Application No. 10-2016-0047838, filed on Apr. 19, 2016, Korean Patent Application No. 10-2017-0049881, filed on Apr. 18, 2017 and International Patent Application No. PCT/KR2017/004182, filed on Apr. 19, 2017, the disclosure of which is incorporated herein by reference in its entirety.

TECHNICAL FIELD

The present invention relates to a coenzyme Q10 solubilizing composition that enhances the water solubility of coenzyme Q10, which is a poorly water-soluble drug, and a method of preparing the same.

BACKGROUND ART

Coenzyme Q10, which is referred to as ubiquinone or ubidecarenone and is a poorly water-soluble drug and a physiologically active substance, is known to not only have biological activity as a kind of coenzyme, but also play an important role in ATP production by being located in the electron transport system of the mitochondria, which is an intracellular energy producing organ, and it is widely distributed in the human body to reduce blood glucose by converting sugar to energy, and like vitamin E, it acts as an antioxidant, preventing cell membranes from being oxidized and increasing an oxygen utilization rate.

Coenzyme Q10 has been reported to protect cells from harmful oxygen and have an excellent effect as an antioxidant that helps the activity of vitamin E with an antioxidant function, thereby having antioxidant function-induced effects such as anti-cancer prevention, aging prevention, and blood low density lipoprotein (LDL) oxidation inhibition, and is also known to have an effect as an adjuvant on cardiovascular diseases such as congestive heart failure, angina pectoris, hypertension, heart disease, and the like. In addition, according to a clinical trial report, coenzyme Q10 delays functional degradation in various neurodegenerative diseases such as Huntington' disease, Friedreich's ataxia, especially in Parkinson's disease. In addition, coenzyme Q10 also has an effect of alleviating rheumatic valve diseases and alveolar inflammation through immune function enhancement, and has been developed as drugs due to the above-described various effects. In particular, it has recently been possible to use coenzyme Q10 in health functional foods, and thus usefulness thereof is increasing.

However, coenzyme Q10 has problems such as very low versatility thereof in the use in a drug, a health functional food, or a food because coenzyme Q10 is a poorly water-soluble substance with a very low solubility in water, and to address the problem that applications of coenzyme Q10 to a water-soluble liquid such as beverages are particularly highly limited, coenzyme Q10 is dissolved in a hydrophobic lipid such as an omega-3 fatty acid for oral administration, but has low bioavailability.

Poorly water-soluble drugs refer to drugs that are not readily soluble in water due to inclusion of a structurally hydrophobic part of a compound, and there are many cases in which the practical use of poorly water-soluble drugs is limited due to poor water solubility thereof. For example, approximately 41% or more of drugs developed as new drugs are abandoned in the middle of development due to poor water solubility thereof, and about one third or more of the drugs listed in the US Pharmacopeia are classified as poorly water-soluble drugs.

To use these poorly water-soluble drugs, it is required that additional materials for addressing the poor water solubility be added, but many cases in which the use of poorly water-soluble drugs is limited due to the toxicity of added materials have been reported. For example, generally, to solubilize a poorly water-soluble material, emulsification using an emulsifying agent, capturing using liposomes, and the like are widely used, but the use thereof is limited due to introduction of foreign substances not originating from the human body, physical instability, and the like.

Thus, to apply coenzyme Q10 to drugs, food, and cosmetics, it is necessary to make an effort to maintain a homogeneous aqueous solution state by preventing degeneration according to temperature, storage location, and duration and securing long-term stability, and since this process should be performed without using excessively large amounts of an emulsifying agent, a stabilizer, and an excipient, it requires more enhanced stability.

Due to the characteristics of coenzyme Q10, many studies (Korean Patent Registration No. 10-0871050) have been carried out on solubilization in water or enhancement of bioavailability to apply coenzyme Q10 to beverages and drugs, but no remarkable achievements have not been made.

DISCLOSURE

Technical Problem

The inventors of the present invention had enhanced the water solubility of coenzyme Q10 by encapsulating the coenzyme Q10, which is a poorly water-soluble drug, in a micelle including glycyrrhizic acid or a salt thereof, a bile acid or a salt thereof, and an unsaturated fatty acid, and had enhanced the encapsulation efficiency thereof, thus completing the present invention relating to a coenzyme Q10 solubilizing composition and a method of preparing the same, based on these findings.

Therefore, an object of the present invention is to provide a coenzyme Q10 solubilizing composition characterized in that coenzyme Q10 is encapsulated in a micelle including glycyrrhizic acid or a salt thereof, a bile acid or a salt thereof, and an unsaturated fatty acid.

In addition, another object of the present invention is to provide a method of preparing a coenzyme Q10 solubilizing composition, including: (1) a suspension preparation process of preparing a suspension by adding glycyrrhizic acid or a salt thereof, a bile acid or a salt thereof, an unsaturated fatty acid, and coenzyme Q10 to a solvent and then stirring the resulting solution; and (2) a homogenizing process of homogenizing the suspension by sonication or using a microfluidizer.

However, technical objects to be achieved by the present invention are not limited to the above-described objects, and other unmentioned objects will become apparent from the following description to those of ordinary skill in the art.

Technical Solution

The present invention provides a coenzyme Q10 solubilizing composition characterized in that coenzyme Q10 is encapsulated in a micelle including glycyrrhizic acid or a salt thereof, a bile acid or a salt thereof, and an unsaturated fatty acid.

In one embodiment of the present invention, the coenzyme Q10 solubilizing composition may further include ascorbic acid.

In another embodiment of the present invention, the bile acid may be any one or more selected from the group consisting of cholic acid, deoxycholic acid, and ursodeoxycholic acid.

In another embodiment of the present invention, the unsaturated fatty acid may be any one or more selected from the group consisting of an omega-3 fatty acid, myristoleic acid, palmitoleic acid, oleic acid, alpha-linolenic acid, gamma-linolenic acid, linolenic acid, conjugated linoleic acid, and arachidonic acid.

In another embodiment of the present invention, the omega-3 fatty acid may be eicosapentaenoic acid (EPA) or docosahexaenoic acid (DHA).

In another embodiment of the present invention, in the coenzyme Q10 solubilizing composition, an amount of the coenzyme Q10 to be encapsulated may range from 1 wt % to 50 wt % with respect to a total weight of the composition.

In another embodiment of the present invention, the coenzyme Q10 solubilizing composition may include coenzyme Q10 at a concentration of 0.05 mg/mL to 3 mg/mL.

In another embodiment of the present invention, a mixing ratio of the glycyrrhizic acid or a salt thereof, the bile acid or a salt thereof, the unsaturated fatty acid, and the coenzyme Q10 may be 0.1 to 5:0.1 to 5:0.1 to 5:0.1 to 5 on a weight basis.

In another embodiment of the present invention, the coenzyme Q10 solubilizing composition may have a particle size of 10 nm to 200 nm.

In another embodiment of the present invention, the composition may be a pharmaceutical composition.

In another embodiment of the present invention, the composition may be a food composition.

In another embodiment of the present invention, the composition may be a cosmetic composition.

According to an aspect of another embodiment, there is provided a method of preparing a coenzyme Q10 solubilizing composition, including: (1) a suspension preparation process of preparing a suspension by adding glycyrrhizic acid or a salt thereof, a bile acid or a salt thereof, an unsaturated fatty acid, and coenzyme Q10 to a solvent and then stirring the resulting solution; and (2) a homogenizing process of homogenizing the suspension by sonication or by using a microfluidizer.

In one embodiment of the present invention, the method of preparing a coenzyme Q10 solubilizing composition may further include (3) a process of purifying the coenzyme Q10 solubilizing composition prepared by the homogenization (process (2)) through a filter.

In one embodiment of the present invention, the method of preparing a coenzyme Q10 solubilizing composition may further include (4) a purification process of purifying the coenzyme Q10 solubilizing composition, which is present in the form of a filtrate obtained by the purification (process (3)), through a filter after storage at 0° C. to 5° C.

In another embodiment of the present invention, the suspension may further include ascorbic acid.

Advantageous Effects

In a coenzyme Q10 solubilizing composition and a method of preparing the same according to the present invention, coenzyme Q10, which is a poorly water-soluble drug, is encapsulated in a micelle including glycyrrhizic acid or a salt thereof, a bile acid (cholic acid, deoxycholic acid, or ursodeoxycholic acid), and an unsaturated fatty acid, thereby enhancing the encapsulation efficiency and water solubility of coenzyme Q10. In addition, a micelle in which ascorbic acid having an excellent collagen synthesis promoting effect, an excellent UV-blocking effect, an excellent antioxidant effect, and an excellent melanin production inhibitory effect is included is prepared for the composition, thereby imparting functionality to the bioavailability of the prepared composition. The composition can be readily mass-produced by sonication or by using a microfluidizer, a particle size of the composition that encapsulates coenzyme Q10 can be adjusted, natural substance-based formulation without using ethanol and an organic solvent can be performed, and it is anticipated that the composition will be usefully used as pharmaceutical, food and cosmetic compositions that have almost no toxicity and secured stability.

In addition, according to the present invention, coenzyme Q10 and/or an unsaturated fatty acid, which are/is known to have low bioavailability due to low water solubility and poor absorption in the gastrointestinal tract while having various physiological activities such as anti-inflammatory action, and the like, are/is solubilized to enhance pharmacokinetic (PK) properties, and pharmaceutical application of the composition in the corresponding field is anticipated.

DESCRIPTION OF DRAWINGS

FIG. 2 illustrates a method of preparing a coenzyme Q10 solubilizing composition by sonication, wherein

FIG. 8 illustrates surface charge analysis results of a coenzyme Q10 solubilizing composition prepared by sonication.

FIG. 10 illustrates particle size distribution analysis results of a coenzyme Q10 solubilizing composition prepared by sonication (left image) and of the composition under autoclaving conditions (right image).

FIG. 11 illustrates a method of preparing a coenzyme Q10 solubilizing composition using a microfluidizer, wherein

BEST MODE

Figure 1:
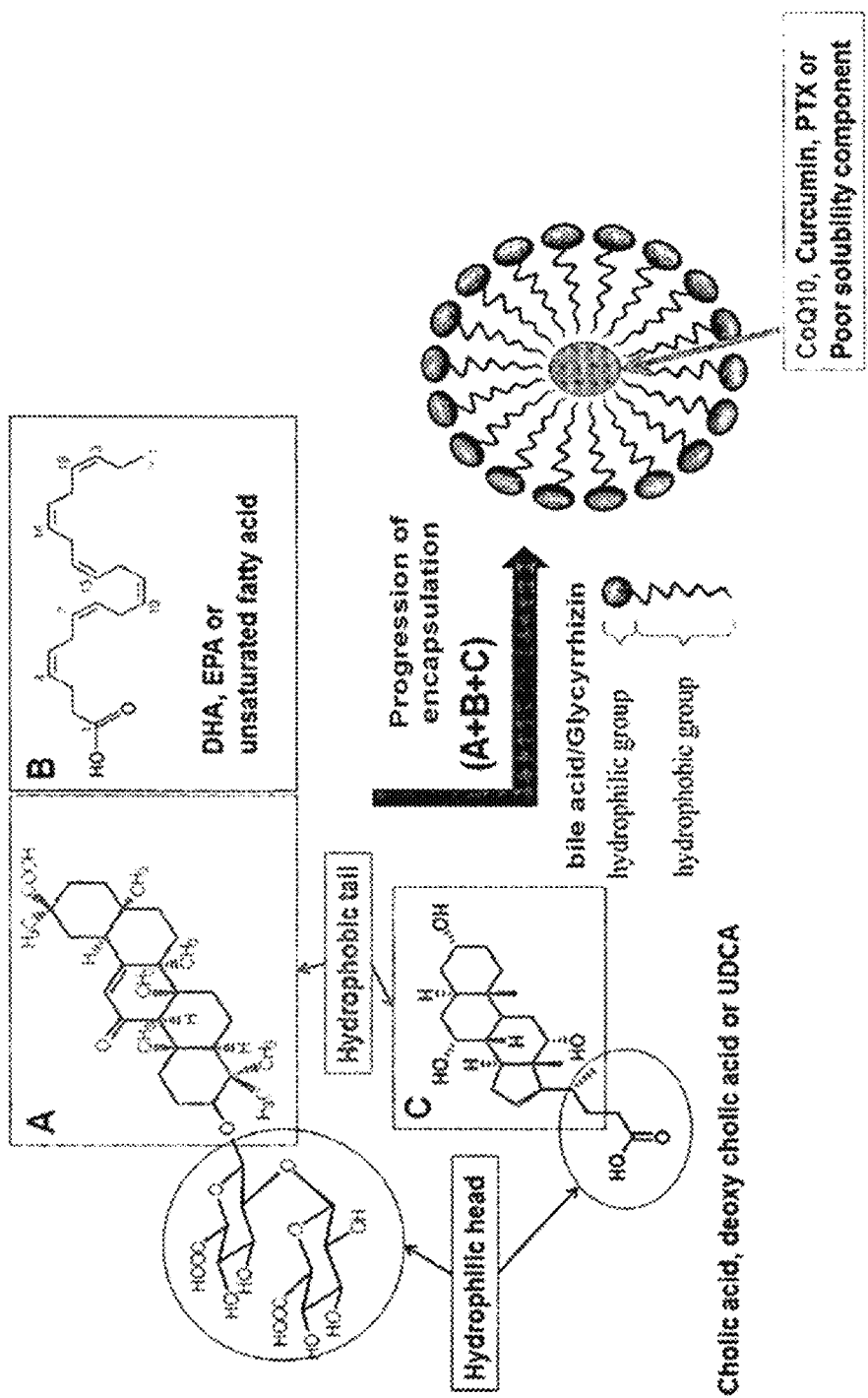
FIG. 1 illustrates the formation of a micelle of a coenzyme Q10 solubilizing composition consisting of glycyrrhizin, a bile acid (cholic acid, deoxycholic acid, or ursodeoxycholic acid), an unsaturated fatty acid, and coenzyme Q10.

The present invention relates to a coenzyme Q10 solubilizing composition and a method of preparing the same, and when coenzyme Q10 was encapsulated in a micelle including glycyrrhizic acid or a salt thereof, a bile acid or a salt thereof, and an unsaturated fatty acid, the water solubility of coenzyme Q10, which is a poorly water-soluble drug, was enhanced and the encapsulation efficiency thereof was enhanced, thus the present invention was completed based on these findings.

Hereinafter, the present invention will be described in detail.

The present invention provides a coenzyme Q10 solubilizing composition characterized in that coenzyme Q10 is encapsulated in a micelle including glycyrrhizic acid or a salt thereof, a bile acid or a salt thereof, and an unsaturated fatty acid.

In the present invention, the bile acid may be any one or more selected from the group consisting of cholic acid, deoxycholic acid, and ursodeoxycholic acid, but the present invention is not limited to the above examples.

In the present invention, the unsaturated fatty acid may be an omega-3 fatty acid, myristoleic acid, palmitoleic acid, oleic acid, alpha-linolenic acid, gamma-linolenic acid, linolenic acid, conjugated linoleic acid, or arachidonic acid and is preferably an omega-3 fatty acid, but the present invention is not limited thereto. In addition, the omega-3 fatty acid may be any one or more selected from the group consisting of eicosapentaenoic acid (EPA) and docosahexaenoic acid (DHA), but the present invention is not limited thereto. More particularly, in the coenzyme Q10 solubilizing composition, a bile acid, an omega-3 fatty acid, and glycyrrhizin, which are materials derived from natural substances, form a micelle and thus are used as excipients or stabilizers for the solubilization of coenzyme Q10, and since ethanol or an organic solvent is not used as an excipient or a stabilizer, natural substance-based formulation is possible and the composition has almost no toxicity.

The term "excipient" as used herein refers to a substance added to a drug or a food for the purpose of imparting a suitable form to the drug or food or increasing the amount thereof for convenience of use, and the term "stabilizer" as used herein refers to a substance used to prevent degeneration of a drug or a food. Thus, the coenzyme Q10 solubilizing composition of the present invention may exhibit enhanced solubility by including the natural substance-derived biostable material such as a bile acid, an omega-3 fatty acid, or glycyrrhizin, and may exhibit enhanced long-term stability.

In addition, the amount of coenzyme Q10 encapsulated in the coenzyme Q10 solubilizing composition may range from 15 wt % to 40 wt % with respect to a total weight of the composition, but the present invention is not limited thereto.

In addition, in the coenzyme Q10 solubilizing composition, coenzyme Q10 may be included at a concentration of 0.05 mg/mL to 3 mg/mL in an aqueous coenzyme Q10 solubilizing composition solution, but the present invention is not limited thereto.

In addition, a mixing ratio of the glycyrrhizic acid or a salt thereof, the bile acid, the omega-3 fatty acid, and the coenzyme Q10 may be 0.1 to 5:0.1 to 5:0.1 to 5:0.1 to 5, preferably 0.1 to 5:1:1:1, on a weight basis, but the present invention is not limited thereto.

In addition, according to one embodiment of the present invention, the coenzyme Q10 solubilizing composition may further include ascorbic acid, and a mixing ratio of the glycyrrhizic acid or a salt thereof, the bile acid, the omega-3 fatty acid, the ascorbic acid, and the coenzyme Q10 may be preferably 0.1 to 5:0.1 to 5:0.1 to 5:0.1 to 5:0.1 to 5, more preferably 6:2:2:2:1, on a weight basis, but the present invention is not limited thereto.

In addition, in the coenzyme Q10 solubilizing composition including ascorbic acid, ascorbic acid may be included in the aqueous coenzyme Q10 solubilizing composition solution including ascorbic acid at a concentration of 0.05 mg/mL to 3 mg/mL, but the present invention is not limited thereto.

In addition, the coenzyme Q10 solubilizing composition may have a particle size of 10 nm to 200 nm, but the present invention is not limited thereto. More particularly, the particle size of the coenzyme Q10 solubilizing composition may be adjusted through the concentration of the glycyrrhizic acid.

In addition, the coenzyme Q10 solubilizing composition may be a pharmaceutical composition.

Coenzyme Q10 is a substance which is primarily found in the mitochondria, which is an energy-producing organ of cells, and is widely distributed in the human body. Coenzyme Q10, which is an antioxidant that protects cells from harmful oxygen and helps the activity of vitamin E with an antioxidant function, is known to have excellent effects such as aging prevention, anti-inflammation, invigoration, and immune system enhancement, and the like, and also known to have an effect as an adjuvant on a cardiovascular disease such as congestive heart failure, angina pectoris, hypertension, or the like. In addition, according to a clinical trial report, coenzyme Q10 delays functional degradation in various neurodegenerative diseases such as Huntington' disease, Friedreich's ataxia, especially Parkinson's disease.

Thus, the coenzyme Q10 solubilizing composition of the present invention is not limited to only a pharmaceutical composition for the prevention, alleviation, or treatment of a specific disease, and may be used as an additional active ingredient in a drug. For example, the coenzyme Q10 solubilizing composition may be used as a composition effective in heart disease, hypertension, rheumatic valve disease, alveolar inflammation, congestive heart failure, and cerebrovascular disorders, and against side effects of anticancer drugs (cardiac dysfunction by adriamycin), but the present invention is not limited thereto.

The pharmaceutical composition according to the present invention may include a pharmaceutically acceptable carrier in addition to the active ingredient. In this regard, the pharmaceutically acceptable carrier is a carrier which is commonly used in formulation, and examples thereof may include lactose, dextrose, sucrose, sorbitol, mannitol, starch, acacia gum, calcium phosphate, alginates, gelatin, calcium silicate, microcrystalline cellulose, polyvinylpyrrolidone, cellulose, water, syrup, methyl cellulose, methylhydroxy benzoate, propylhydroxy benzoate, talc, magnesium stearate, and mineral oil, but the present invention is not limited thereto. In addition, the pharmaceutical composition may further include, in addition to the above-listed ingredients, a lubricant, a wetting agent, a sweetener, a flavoring agent, an emulsifying agent, a suspension agent, a preservative, or the like.

The pharmaceutical composition of the present invention may be formulated into granules, powder, coated tablets, tablets, capsules, suppositories, syrups, juices, suspensions, emulsions, drops, injectable liquids, sustained-release type preparations of an active compound, or the like. In particular, the coenzyme Q10 solubilizing composition of the present invention may be used as a sustained-release type drug since poorly water-soluble coenzyme Q10 encapsulated in a micelle is slowly released.

The pharmaceutical composition of the present invention may be administered orally or parenterally (e.g., intravenously, subcutaneously, intraperitoneally, or locally) according to a desired method, and a suitable dose of the pharmaceutical composition varies according to the conditions and body weight of patients, the severity of diseases, drug form, administration route, and administration time, but may be appropriately selected by those of ordinary skill in the art.

The pharmaceutical composition of the present invention is administered in a pharmaceutically effective amount. The term "pharmaceutically effective amount" as used herein refers to an amount sufficient to treat diseases at a reasonable benefit/risk ratio applicable to medical treatment, and an effective dosage level may be determined according to factors including type of diseases of patients, the severity of disease, the activity of drugs, sensitivity to drugs, administration time, administration routes, excretion rate, treatment periods, and simultaneously used drugs, and other factors well known in medical fields. The pharmaceutical composition according to the present invention may be administered as an individual therapeutic agent or in combination with other therapeutic agents, may be administered consecutively or simultaneously with a conventional therapeutic agent, and may be administered as a single dose or multiple doses. It is important to administer an amount to obtain a maximum effect in a minimum amount without side effects by considering all of the above-described factors, and the amount may be easily determined by one of ordinary skill in the art.

In particular, the effective amount of the pharmaceutical composition of the present invention may vary depending on the age, gender, conditions, and body weight of patients, the absorption of an active ingredient in the body, inactivity, excretion rate, the type of diseases, and drugs used in combination therewith, and generally, the pharmaceutical composition may be administered daily or every other day at a dose of 0.001 mg to 150 mg per body weight (1 kg), preferably 0.01 mg to 100 mg per body weight (1 kg), or it may be administered in one to three divided doses a day. However, the dose may be increased or decreased depending on administration routes, the severity of obesity, gender, body weight, age, and the like, and thus the above-described dose is not intended to limit the scope of the present invention in any way.

The pharmaceutical composition of the present invention may be administered to mammals such as humans, non-human primates, mice, rats, dogs, cats, horses, cows, and the like, but the present invention is not limited thereto.

In addition, the coenzyme Q10 solubilizing composition may be a food composition, and may be added to any type of food without being particularly limited to a specific application. When the coenzyme Q10 solubilizing composition of the present invention is used as a food additive, the compound may be added as is or used in combination with other foods or food ingredients, and it may be appropriately used according to a general method. Mixing amounts of active ingredients may be appropriately determined according to the purpose of use (for prevention, health, or treatment). Generally, when preparing foods or beverages, the compound of the present invention is added in an amount of 15 wt % or less, preferably 10 wt % or less, with respect to the amount of raw materials. However, in the case of long-term administration for health and hygienic purposes or for health control, an amount in the above-described range or less may be used, and the active ingredient may also be used in an amount equal to or greater than the above-described range since there is no problem in terms of safety.

The type of the food is not particularly limited. Examples of foods to which the material may be added include meats, sausages, bread, chocolates, candies, snacks, confectionaries, pizzas, instant noodles, other noodles, gums, dairy products including ice creams, various kinds of soup, beverages, teas, drinks, alcoholic drinks, vitamin complexes, and the like, and all foods in the ordinary sense are included.

When the coenzyme Q10 solubilizing composition of the present invention is used as a health beverage composition, the health beverage composition may include various flavoring agents, natural carbohydrates, or the like as additional ingredients, like general beverages. Examples of the above-described natural carbohydrates include monosaccharides such as glucose and fructose; disaccharides such as maltose and sucrose; polysaccharides such as dextrin and cyclodextrin; and sugar alcohols such as xylitol, sorbitol, erythritol, and the like. Examples of sweeteners may include natural sweeteners such as thaumatin and *stevia* extracts, synthetic sweeteners such as saccharin and aspartame, and the like. The amount of the natural carbohydrate generally ranges from about 0.01 g to about 0.20 g, preferably about 0.04 g to 0.10 g, with respect to 100 ml of the composition of the present invention.

In addition, the composition of the present invention may include various nutrients, vitamins, electrolytes, a flavoring agent, a colorant, pectic acid and a salt thereof, alginic acid and a salt thereof, organic acids, a protective colloidal thickening agent, a pH adjusting agent, a stabilizer, a preservative, glycerin, alcohols, carbonating agents used in carbonated beverages, or the like. In addition, the composition of the present invention may include pulp for preparing natural fruit juices, fruit beverages, vegetable beverages, or the like. These ingredients may be used alone, or a combination of these ingredients may be used. Although the percentage of these additives is not much important, the percentage of these additives is generally selected from the range of 0.01 parts by weight to 0.20 parts by weight with respect to 100 parts by weight of the composition of the present invention.

In addition, the coenzyme Q10 solubilizing composition may be a cosmetic composition.

Since coenzyme Q10 provides effects such as antioxidation, anti-inflammation, invigoration, skin moisturizing, and aging prevention, the coenzyme Q10 solubilizing composition of the present invention may be used as a cosmetic composition, and since a bile acid, an omega-3 fatty acid, or glycyrrhizin are used in the coenzyme Q10 solubilizing composition, the coenzyme Q10 solubilizing composition has excellent biocompatibility through the natural substance-derived biostable materials and thus does not cause skin irritation, and therefore, it is anticipated that the composition will fully provide a skin enhancement effect.

Thus, the cosmetic composition of the present invention may include ingredients commonly used in a cosmetic composition in addition to the coenzyme Q10 solubilizing composition, formulation thereof is not particularly limited, and the composition may be formulated into a skin lotion, a skin softener, a skin toner, an astringent, a lotion, a milk lotion, a moisturizing lotion, a nourishing lotion, a massage cream, a nourishing cream, a moisturizing cream, a hand cream, an essence, a nourishing essence, a pack, a soap, a shampoo, a cleansing foam, a cleansing lotion, a cleansing cream, a body lotion, a body cleanser, an emulsion, a lipstick, a makeup base, a foundation, a press powder, a loose powder, an eye shadow, and the like. These cosmetics may include general ingredients such as aqueous vitamins, oily vitamins, polymer peptides, polymeric polysaccharides, sphingolipids, or the like, and may be easily prepared according to technologies widely known to those of ordinary skill in the art.

In addition, in each dosage form of the cosmetic composition, other ingredients in addition to coenzyme Q10 as skin enhancing raw materials may be appropriately selected and mixed according to the dosage form or purpose of use of cosmetics by those of ordinary skill in the art without undue difficulty. Examples of the other ingredients may include general additives such as an antioxidant, a UV-blocking agent, an exfoliating agent, a surfactant, a flavoring, a coloring, a preservative, a pH adjusting agent, a chelating agent, a stabilizer, a solubilizing agent, vitamins, a pigment, and a flavoring, and a carrier.

According to another embodiment of the present invention, there is provided a method of preparing a coenzyme Q10 solubilizing composition. More particularly, the method may basically include: (1) a suspension preparation process of preparing a suspension by adding glycyrrhizic acid or a salt thereof, a bile acid, an omega-3 fatty acid, and coenzyme Q10 to a solvent and then stirring the resulting solution; and (2) a homogenizing process of homogenizing the suspension by sonication or using a microfluidizer. In the case of a supersaturated micelle, the method may further include (3) a purification process of purifying the coenzyme Q10 solubilizing composition prepared in the homogenizing process, through a filter, and may further include (4) a purification process of purifying the coenzyme Q10 solubilizing composition, which is present in the form of a filtrate obtained in purification process (3), through a filter after storage at 0° C. to 5° C. In a method of preparing a coenzyme Q10 solubilizing composition by sonication, a first step may be performed by dissolving glycyrrhizic acid or a salt thereof, a bile acid, an omega-3 fatty acid, and coenzyme Q10 in distilled water or phosphate buffered saline (PBS) with pH 7.4 and pre-crushing the solution by using ultrasound with a low energy of 300 W, and a second step may be performed by forming a micelle by using ultrasound with a high energy of 500 W. In a third step, the composition prepared in the second step may be purified using a 0.22 μm syringe filter. In a fourth step, the composition purified by the third step may be stored at a low temperature of 0° C. to 5° C., more preferably 4° C., for 12 hours, and then similarly subjected to purification using a 0.22 μm syringe filter, and although the purification process of step 4 may not be performed through optimization of the first step, the second step, and/or the third step, the present invention is not limited thereto.

In a method of preparing a coenzyme Q10 solubilizing composition by using a microfluidizer, a first step may be performed by dissolving a mixture of glycyrrhizic acid or a salt thereof, a bile acid, an omega-3 fatty acid, and coenzyme Q10 in distilled water or phosphate buffered saline (PBS) with pH 7.4 and stirring the solution at 4,000 rpm or more, and a second step may be performed by crushing the solution in a microfluidizer at a high pressure of 800 bars to 2,000 bars (780 atm to 1,970 atm) for 1 hour to thereby form a micelle. In a third step, a supersaturated composition prepared in the second step may be purified using a 0.22 μm syringe filter. In a fourth step, the composition purified by the third step may be stored at a low temperature of 0° C. to 5° C., more preferably 4° C., for 12 hours, and then likewise subjected to purification using a 0.22 μm syringe filter, and although the purification process of step 4 may not be performed through optimization of the first step, the second step, and/or the third step, the present invention is not limited thereto.

In one embodiment of the present invention, a coenzyme Q10 solubilizing composition was prepared by sonication, and the prepared composition was characterized by evaluation of encapsulation efficiency (see Example 1).

In another embodiment of the present invention, a coenzyme Q10 solubilizing composition was prepared by a method of preparing a coenzyme Q10 solubilizing composition for various concentrations of glycyrrhizin, a licorice-derived natural substance, and encapsulation efficiency thereof was evaluated (see Example 2-1). From the coenzyme Q10 solubilizing composition, encapsulated coenzyme Q10 was quantified (see Example 2-2), and the particle size distribution (see Example 2-3) and surface charge (see Example 2-4) of the coenzyme Q10 solubilizing composition were determined.

In another embodiment of the present invention, the stability of the coenzyme Q10 solubilizing composition was confirmed through autoclaving (see Example 3-1), and the particle size distribution of the autoclaved coenzyme Q10 solubilizing composition was determined (see Example 3-2).

In another embodiment of the present invention, to mass produce a coenzyme Q10 solubilizing composition, a coenzyme Q10 solubilizing composition was prepared using a microfluidizer (see Example 4-1), and the particle size distribution of the coenzyme Q10 solubilizing solution was determined (see Examples 4-2 and 4-3), and the coenzyme Q10 solubilizing composition was quantitatively analyzed (see Example 4-4).

When the coenzyme Q10 solubilizing composition and the method of preparing the same are used, it is possible to prepare a solubilizing composition with a high encapsulation efficiency of 0.05% (w/v) to 0.1% (w/v), it is possible to prepare a composition by sonication or easily mass produce a composition by using a microfluidizer, and the prepared composition may be used as pharmaceutical, food, and cosmetic compositions that exhibit increased water solubility and secured stability.

Hereinafter, exemplary embodiments will be described to aid in understanding of the present invention. However, these examples are provided for illustrative purposes only and are not intended to limit the scope of the present invention.

EXAMPLES

Figure 2A:
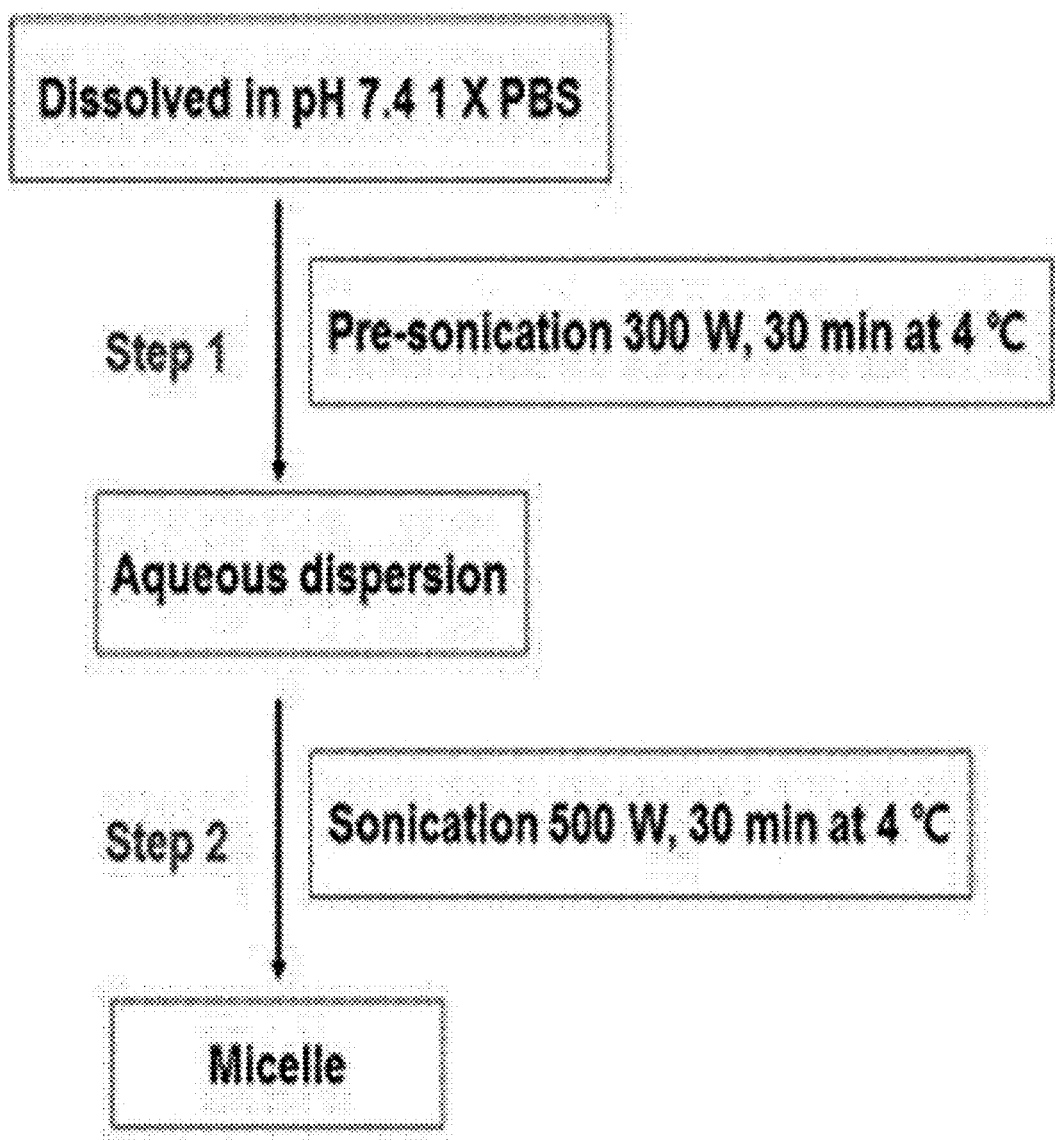
FIG. 2A illustrates a method of preparing coenzyme Q10 solubilizing composition in an unsaturated state.

Example 1. Sonication-Based Preparation and Characterization of Coenzyme Q10 Solubilizing Composition To prepare a coenzyme Q10 solubilizing composition including a high concentration of coenzyme Q10 illustrated in FIG. 1, a preparation method illustrated in FIG. 2 was performed under conditions shown in Table 1 below. More particularly, distilled water was injected into a reactor, and then dipotassium glycyrrhizinate, eicosapentaenoic acid (EPA), and cholic acid for the formation of a micelle, and coenzyme Q10, which is a poorly water-soluble drug, were added in amounts shown in Table 1 below and stirred to a uniform dispersion. The reaction solution was subjected to sonication corresponding to an output of 300 W at 4° C. for 30 minutes to a more uniform dispersion, followed by sonication corresponding to an output of 500 W at 4° C. for 30 minutes to perform the encapsulation of coenzyme Q10 through the formation of a micelle (see FIG. 2A).

Figure 2B:
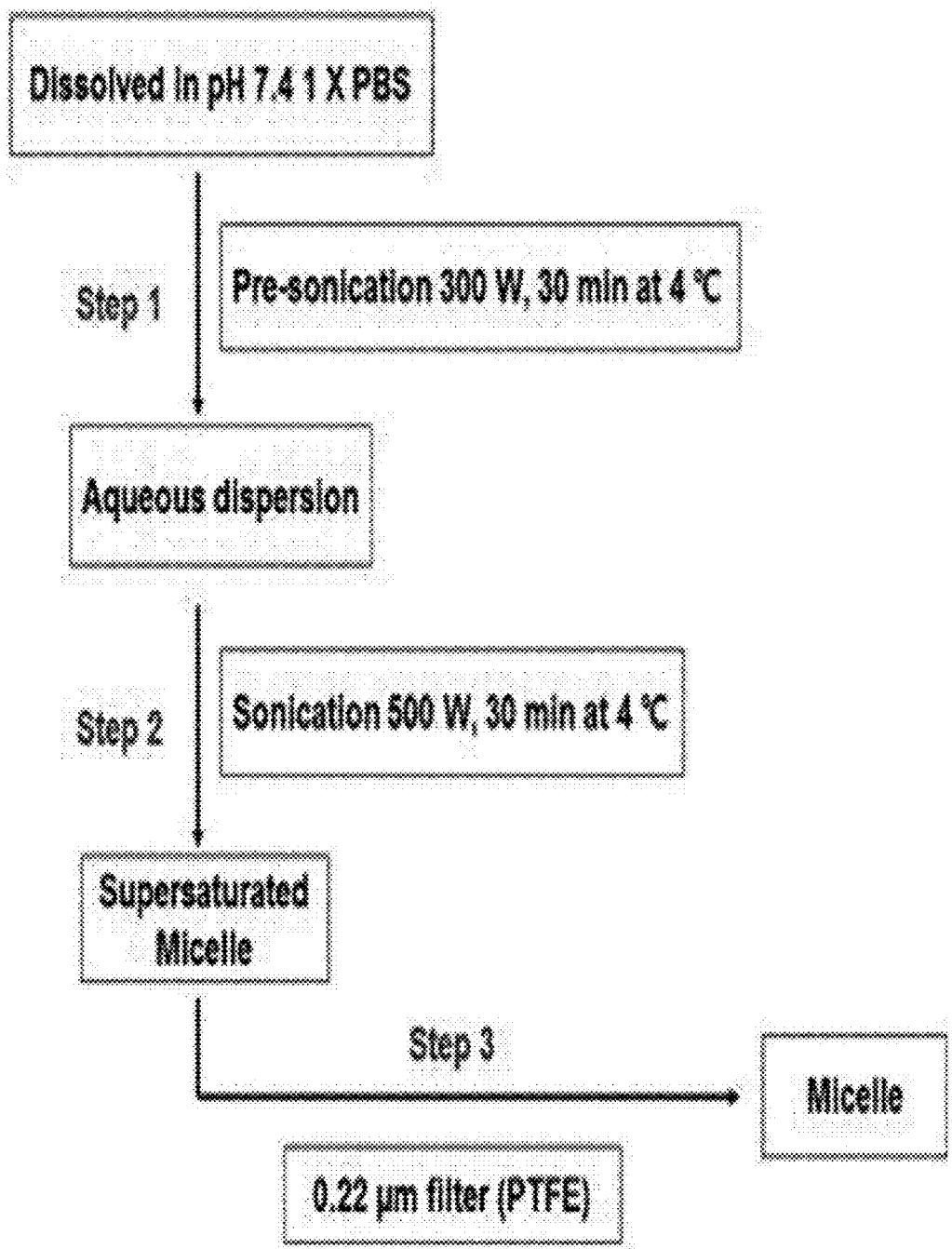
FIG. 2B illustrates a method of preparing a coenzyme Q10 solubilizing composition in a supersaturated state.
Figure 3:
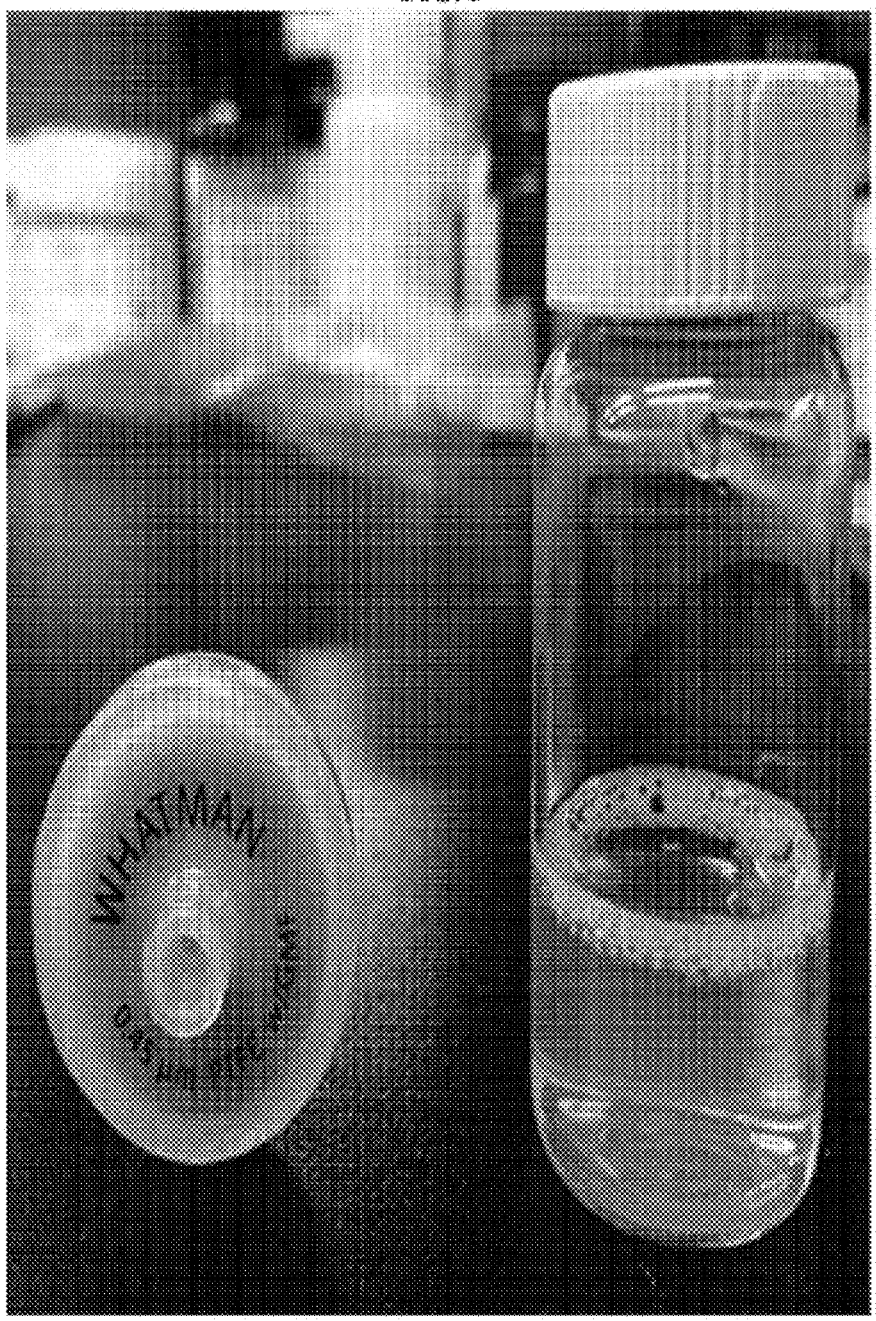
FIG. 3 illustrates a composition that had been subjected to simple filtration after step 2 in a method of preparing a coenzyme Q10 solubilizing composition.
Figure 4:
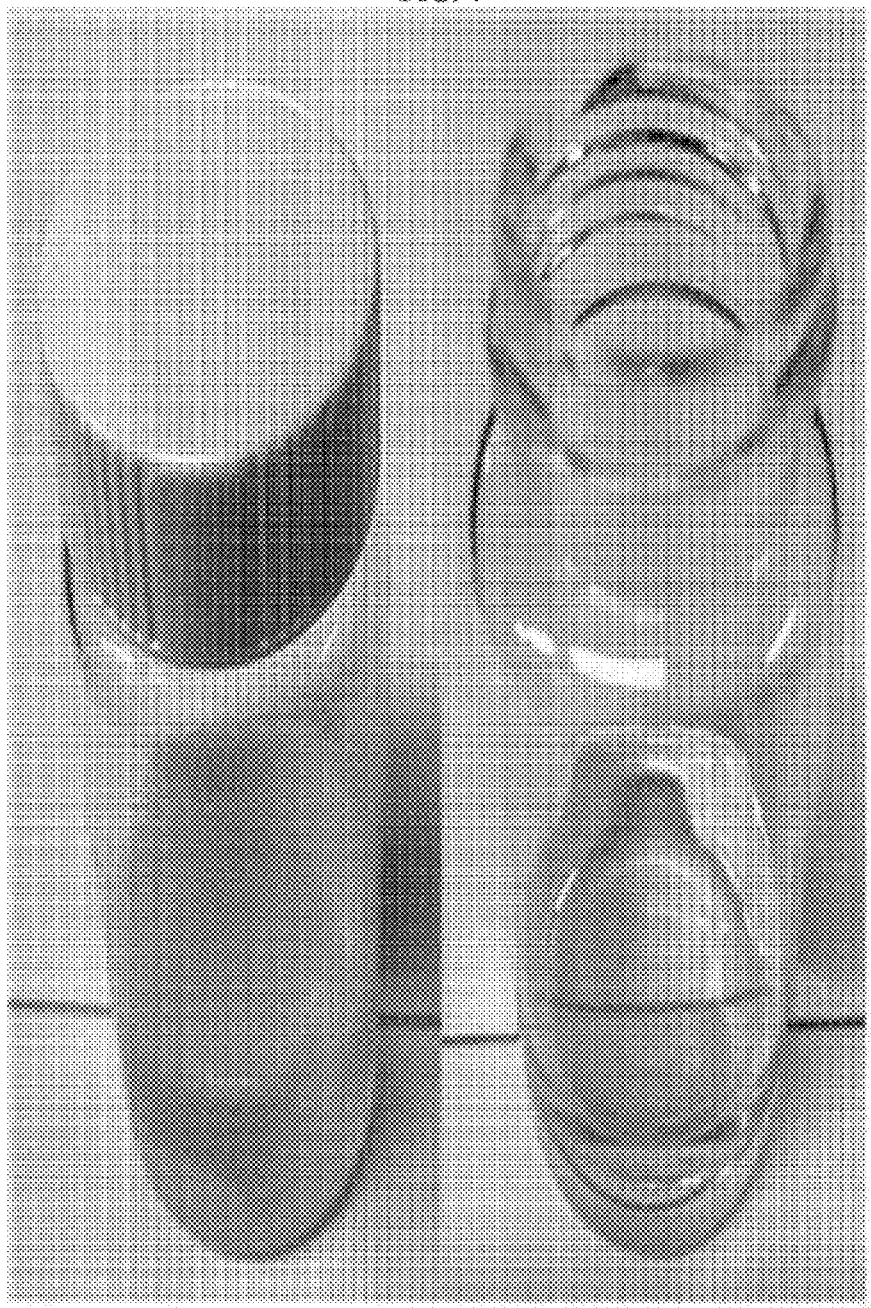
FIG. 4 illustrates an excipient and a stabilizer that, after storage at 4° C. for 12 hours, were unable to form a micelle in a third step of preparing a supersaturated composition of the method of preparing a coenzyme Q10 solubilizing composition (see FIG. 2B) and formed a precipitate (left image), and a coenzyme Q10 solubilizing composition obtained by filtering the precipitate (right image).

At this time, in the case of a supersaturated reaction solution in preparation of the composition, coenzyme Q10 remaining not encapsulated in an aqueous solution was removed using a 0.22 μm syringe filter, and the filtrate was stored at 4° C. for 12 hours and then filtered again using a 0.22 μm syringe filter, followed by cooling and lyophilization at −80° C. for 2 days or more (see FIG. 2B).

As a result, as shown in Table 1 below, powder-type biocompatible micelle particles including coenzyme Q10, which is a poorly water-soluble material, were obtained to prepare a coenzyme Q10 solubilizing composition, and encapsulation efficiency thereof was evaluated.

TABLE 1

| Maximum Solubilization of Coenzyme Q10 (Method: sonication) | | |
|---|---|---|
| Component | Condition A | Condition B |
| CoQ10 | 10 mg | 30 mg |
| Cholic acid | 10 mg | 10 mg |
| EPA | 10 mg | 10 mg |
| Dipotassium glycyrrhizinate | 10 mg | 10 mg |
| Ratio (CoQ10:ChA:EPA:GA) | 1:1:1:1 | 3:1:1:1 |
| Used Solvent | Distilled Water of 10 mL | |
| Content of CoQ10 in total 1 mg of micelle | 0.21 mg | 0.24 mg |

TABLE 1-continued

| Maximum Solubilization of Coenzyme Q10 (Method: sonication) | | |
|---|---|---|
| Component | Condition A | Condition B |
| Yield | 31 mg (78%) | 40 mg (67%) |
| CoQ10 solubilization concentration | 0.65 mg/mL | 0.96 mg/mL |

Example 2. Preparation and Characterization of Coenzyme Q10 Solubilizing Composition for Various Glycyrrhizin Concentrations 2-1. Preparation of Coenzyme Q10 Solubilizing Composition According to Glycyrrhizin Concentration and Evaluation of Encapsulation Efficiency To prepare a coenzyme Q10 solubilizing composition according to the concentration of glycyrrhizin, the preparation method illustrated in FIG. 2 was performed. More particularly, phosphate buffered saline (PBS) was injected into a reactor, and then glycyrrhizin, eicosapentaenoic acid (EPA), and cholic acid for the formation of a micelle, and coenzyme Q10, which is a poorly water-soluble drug, were added in amounts shown in Table 2 below and stirred to a uniform dispersion. The reaction solution was subjected to sonication corresponding to an output of 300 W at 4° C. for 30 minutes to a more uniform dispersion, followed by sonication corresponding to an output of 500 W at 4° C. for 30 minutes to perform the encapsulation of coenzyme Q10 through the formation of a micelle (see FIG. 2A).

In the case of a supersaturated reaction solution in preparation of the composition, coenzyme Q10 remaining not encapsulated in an aqueous solution was removed using a 0.22 μm syringe filter, and the filtrate was stored at 4° C. for 12 hours and then filtered again using a 0.22 μm syringe filter, followed by cooling and lyophilization at −80° C. for 2 days or more, thereby completing the preparation of a coenzyme Q10 solubilizing composition (see FIG. 2B).

As a result, as shown in Table 2 below, powder-type biocompatible micelle particles including coenzyme Q10, which is a poorly water-soluble material, were obtained, and the encapsulation efficiency of the coenzyme Q10 solubilizing composition was evaluated.

TABLE 2

| Component | No. 1 | No. 2 | No. 3 |
|---|---|---|---|
| CoQ10 | 10 mg | 10 mg | 10 mg |
| EPA | 10 mg | 10 mg | 10 mg |
| Cholic acid (ChA) | 10 mg | 10 mg | 10 mg |
| Glycyrrhizic acid (GA) | 50 mg | 30 mg | 10 mg |
| Ratio (CoQ10:EPA:ChA:GA) | 1:1:1:5 | 1:1:1:3 | 1:1:1:1 |
| Size (nm) | 65 | 80 | 105 |
| PDI | 0.061 | 0.095 | 0.155 |
| Zeta potential (mV) | −48.1 | −60.8 | −57.9 |
| Content of CoQ10 in total 1 mg of micelle | 0.22 mg | 0.18 mg | 0.23 mg |

Figure 5:
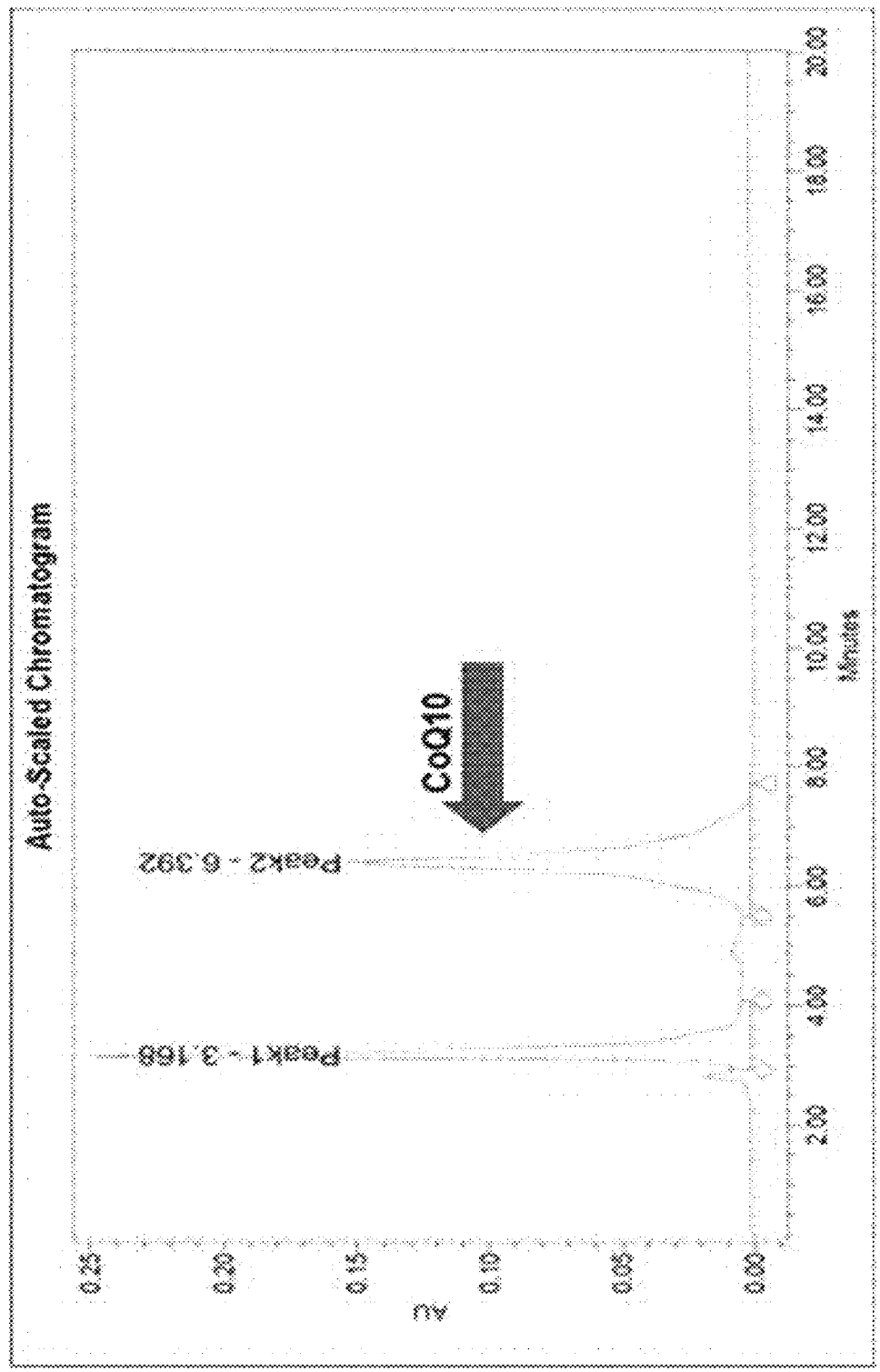
FIG. 5 is a quantitative graph of coenzyme Q10 showing HPLC analysis results of a coenzyme Q10 solubilizing composition prepared by sonication.

2-2. Quantification of Coenzyme Q10 of Coenzyme Q10 Solubilizing Composition for Various Glycyrrhizin Concentrations To quantify coenzyme Q10 from the coenzyme Q10 solubilizing composition prepared by the method shown in Table 2 of Example 2-1, a quantitative graph of coenzyme Q10 was plotted through HPLC analysis with absorbance at 210 nm. The HPLC analysis was performed using a Waters 2695 HPLC model manufactured by Waters and an Xbridge C18 (4.6×250 mm, 5 µm; Waters) as a column and by constantly flowing a liquid mixture of methanol:isopropanol (40:60) as a mobile-phase solvent at a flow rate of 1 mL/min. As a result, a quantitative graph of coenzyme Q10 of FIG. 5 was obtained.

Figure 6:
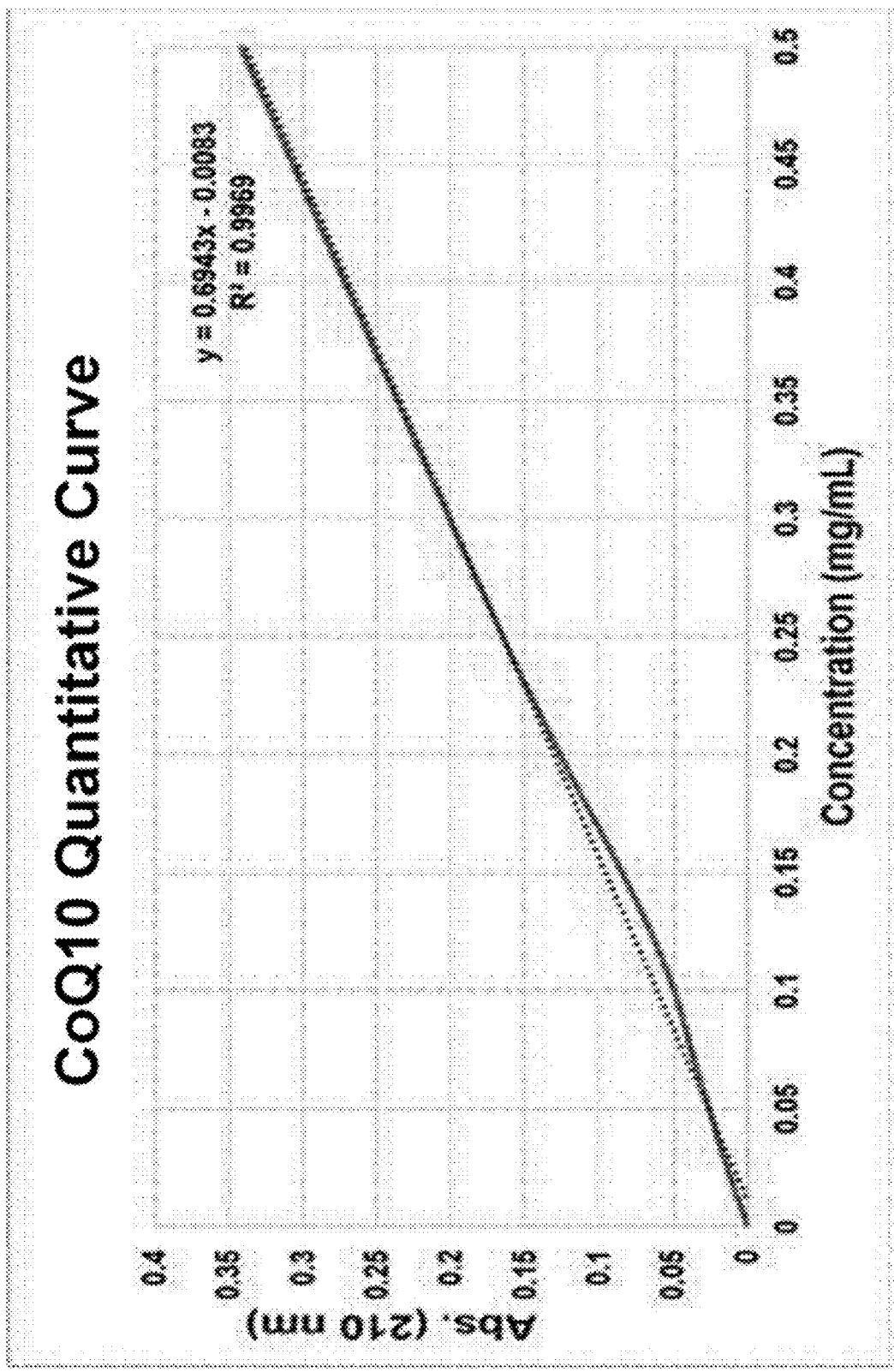
FIG. 6 is a quantitative graph of coenzyme Q10 showing HPLC analysis results of coenzyme Q10 at various concentrations.

In addition, 1 mg of the coenzyme Q10 solubilizing composition was dissolved in alcohol to elute coenzyme Q10 therefrom, and then coenzyme Q10 encapsulated in the coenzyme Q10 solubilizing composition was quantified through HPLC analysis. As a result, a coenzyme Q10 graph of FIG. 6 was obtained.

2-3. Determination of Particle Size Distribution of Coenzyme Q10 Solubilizing Composition for Various Glycyrrhizin Concentrations The particle size distribution of the coenzyme Q10 solubilizing composition prepared by the method of Table 2 of Example 2-1 was measured three times at room temperature using Nano ZS90 equipment manufactured by MALVERN, and then the particle size distribution of the coenzyme Q10 solubilizing composition was analyzed.

Figure 7:
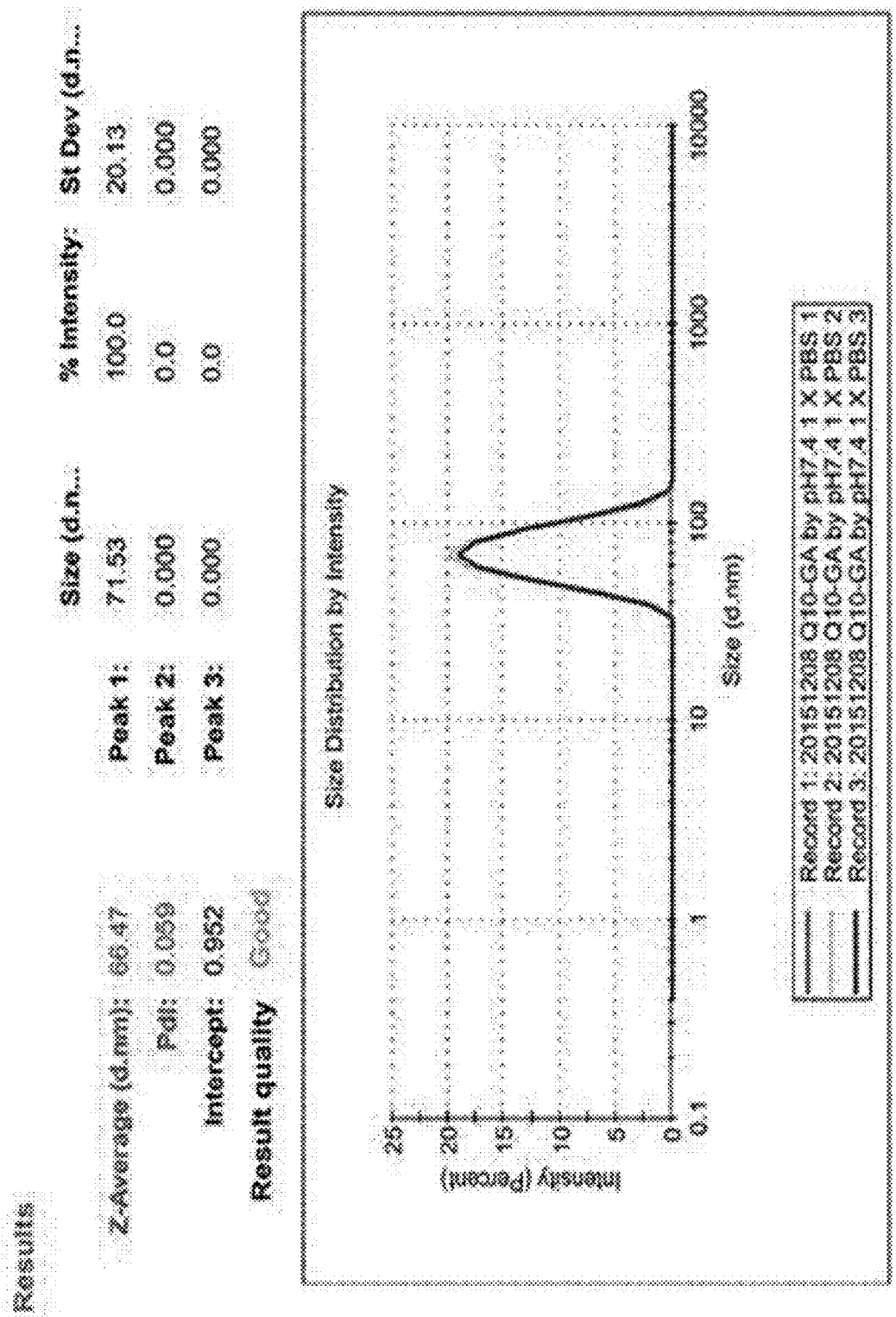
FIG. 7 illustrates particle size distribution analysis results of a coenzyme Q10 solubilizing composition prepared by sonication.

As a result, as illustrated in FIG. 7, uniform particles were identified even after three runs of repeated measurements.

2-4. Determination of Surface Charge of Coenzyme Q10 Solubilizing Composition for Various Glycyrrhizin Concentrations The surface charge measurement of the coenzyme Q10 solubilizing composition was performed for samples according to Table 2 (for each condition) of Example 2-1 at room temperature using Nano ZS90 manufactured by MALVERN, followed by surface charge analysis of the coenzyme Q10 solubilizing composition.

As a result, as illustrated in FIG. 8, it was confirmed that particle surfaces of the coenzyme Q10 solubilizing composition were strongly negatively charged.

Example 3. Verification of Stability of Coenzyme Q10 Solubilizing Composition 3-1. Verification of Stability of Coenzyme Q10 Solubilizing Composition Through Autoclaving A coenzyme Q10 solubilizing composition was prepared using the preparation method illustrated in FIG. 2 under condition A of Table 1 described in Example 1 above, consisting of 10 mL of distilled water, 10 mg of dipotassium glycyrrhizinate, and a ratio of coenzyme Q10:EPA:cholic acid:dipotassium glycyrrhizinate of 1:1:1:1. To verify the stability of the prepared coenzyme Q10 solubilizing composition, autoclaving was performed thereon at a high temperature of 120° C. for 15 minutes.

Figure 9:
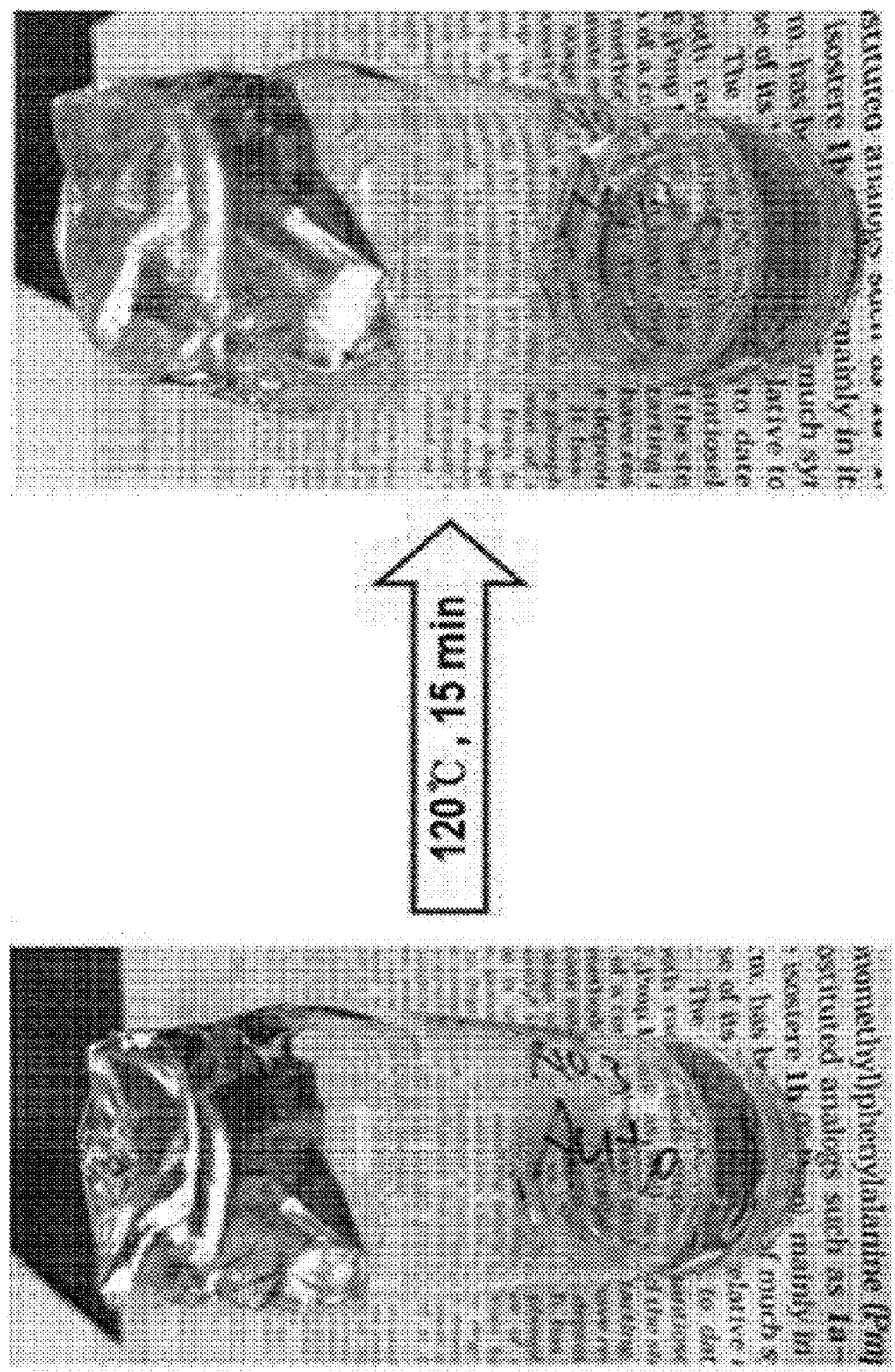
FIG. 9 illustrates a coenzyme Q10 solubilizing composition prepared by sonication (left image) and results of verifying the stability thereof under autoclaving conditions (right image).

As a result, as illustrated in FIG. 9, the coenzyme Q10 solubilizing composition was not precipitated before and after autoclaving, thereby confirming the stability of the coenzyme Q10 solubilizing composition through autoclaving.

3-2. Determination of Particle Size Distribution of Autoclaved Coenzyme Q10 Solubilizing Composition The particle size distribution of the autoclaved coenzyme Q10 solubilizing composition prepared using the method described in Example 3-1 was analyzed using Nano ZS90 equipment manufactured by MALVERN.

As a result, as illustrated in FIG. 10, it was confirmed that the autoclaved coenzyme Q10 solubilizing composition had a particle size of about 20 nm, which was not significantly different from the uniform particle size of the coenzyme Q10 solubilizing composition before autoclaving of about 10 nm, from which it was confirmed that the prepared composition had high stability.

Example 4. Microfluidizer-Based Mass Production and Characterization of Coenzyme Q10 Solubilizing Composition 4-1. Mass Production of Coenzyme Q10 Solubilizing Composition Using Microfluidizer To mass produce a coenzyme Q10 solubilizing composition including a high concentration of coenzyme Q10, a preparation method illustrated in FIG. 11 was performed. More particularly, distilled water was injected into a reactor, and then dipotassium glycyrrhizinate, eicosapentaenoic acid (EPA), and cholic acid for the formation of a micelle, and coenzyme Q10, which is a poorly water-soluble drug, were added in amounts of 10 mg each (1:1:1:1) and stirred at 4,000 rpm to a uniform dispersion. The encapsulation of coenzyme Q10 in the reaction solution was performed through the formation of a micelle by using an APV-2000 microfluidizer manufactured by APV at a high pressure of 1,500 bars for 1 hour, and a micelle was obtained using a 0.22 µm syringe filter. At this time, in the case of the composition in a supersaturated state, coenzyme Q10 remaining not encapsulated in an aqueous solution after solubilizing the composition by using a microfluidizer was removed using a 0.22 µm syringe filter, and the filtrate was stored at 4° C. for 12 hours and then filtered again using a 0.22 µm syringe filter, followed by storage at a low temperature of 4° C.

Figure 12:
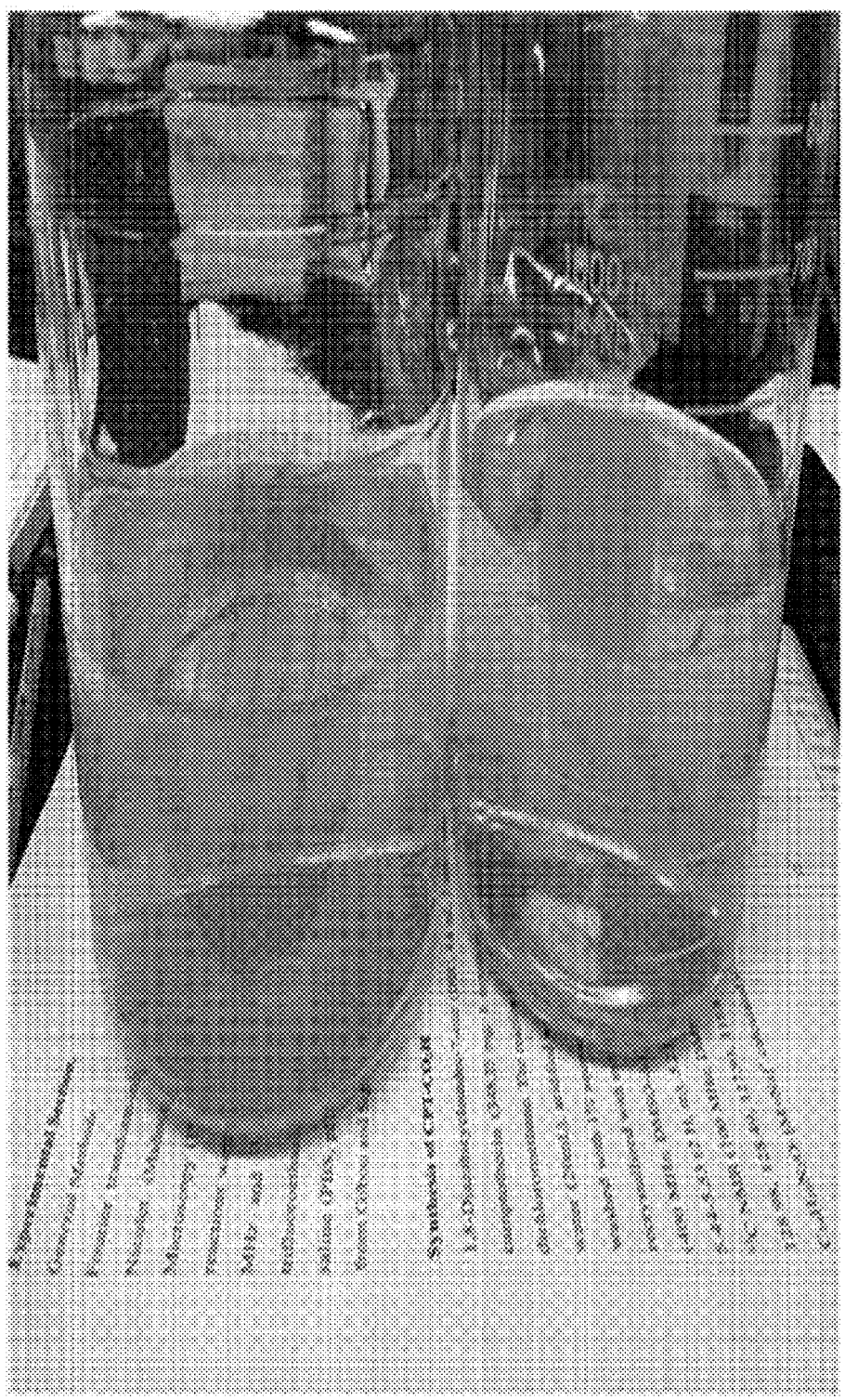
FIG. 12 illustrates a coenzyme Q10 solubilizing composition prepared using a microfluidizer.

As a result, as illustrated in FIG. 12, a coenzyme Q10 solubilizing composition including coenzyme Q10, which is a poorly water-soluble material, was obtained.

4-2. Determination of Particle Size Distribution of Coenzyme Q10 Solubilizing Composition Using Microfluidizer The particle size distribution of the coenzyme Q10 solubilizing composition prepared using the method described in Example 4-1 was analyzed. A microfluidizer was used for the purpose of mass production, and measurement was performed using Nano ZS90 equipment manufactured by MALVERN.

Figure 13:
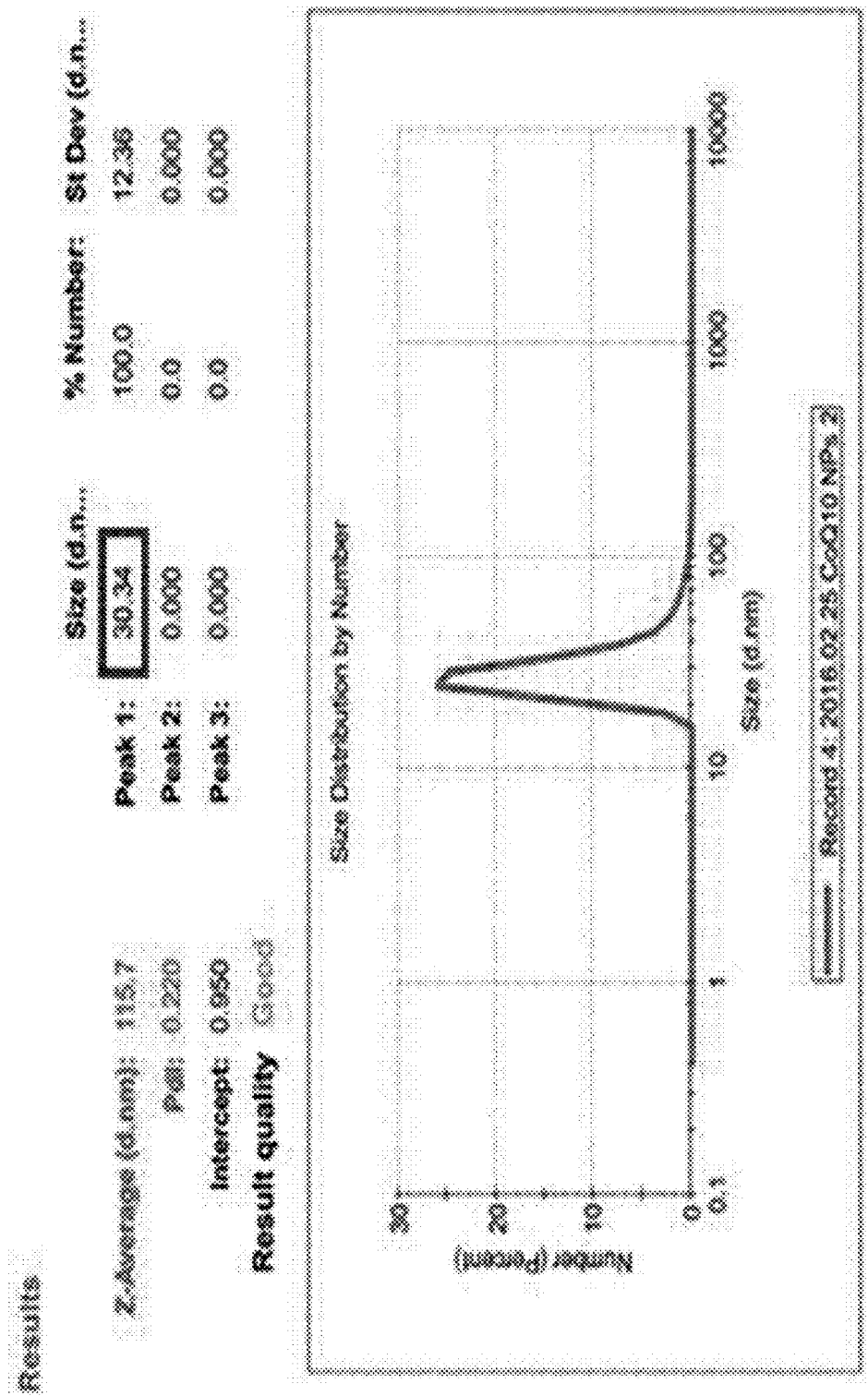
FIG. 13 illustrates particle size distribution analysis results of a coenzyme Q10 solubilizing composition prepared using a microfluidizer.

As a result, as illustrated in FIG. 13, it was confirmed that the coenzyme Q10 solubilizing composition had a uniform particle size of about 30 nm.

4-3. Transmission Electron Microscopic Analysis of Water-Soluble Coenzyme Q10

The particle size of the coenzyme Q10 solubilizing composition prepared using the method described in Example 4-1 was analyzed through a transmission electron microscope, which is more precise equipment than a particle size analyzer.

Figure 14:
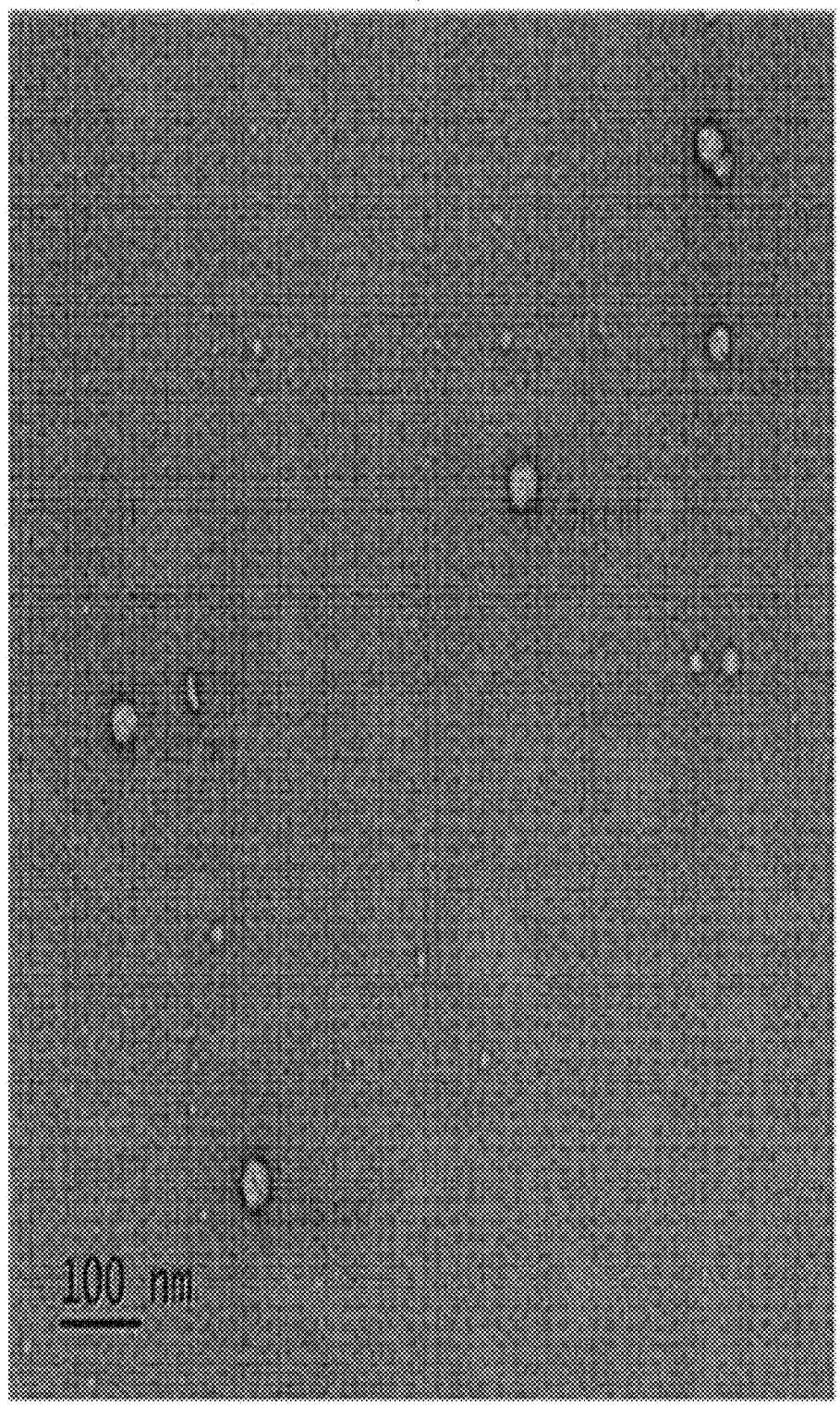
FIG. 14 is a transmission electron microscopic image showing particle size analysis results of a coenzyme Q10 solubilizing composition prepared using a microfluidizer.

As a result, as illustrated in FIG. 14, it was confirmed that the coenzyme Q10 solubilizing composition had a particle size of about 30 nm, which was the same as the result illustrated in FIG. 13 obtained using a particle size analyzer. Since the particle size was determined by the two types of equipment, it is a highly reliable result.

4-4. Quantification of Coenzyme Q10 Solubilizing Composition Prepared Using Microfluidizer The quantification of coenzyme Q10 was performed in 6.2 g/L of the coenzyme Q10 solubilizing composition prepared by the method described in Example 4-1 above using glycyrrhizic acid, coenzyme Q10, eicosapentaenoic acid, cholic acid (3.6 g: 1.2 g: 1.2 mL: 0.6 g), and 1 L of distilled water. In this case, the above-described conditions are optimum conditions in preparation of a coenzyme Q10 solubilizing composition in accordance with the ratio of glycyrrhizic acid:coenzyme Q10:eicosapentaenoic acid:cholic acid of 0.1 to 5:0.1 to 5:0.1 to 5:0.1 to 5, and a range in which the raw materials are mixed may be changed based on Example 2-1 above and Example 4-1 above.

More particularly, 1 mg of the coenzyme Q10 solubilizing composition prepared using the above method was dissolved in 1 mL of an alcohol to elute coenzyme Q10 therefrom, and then coenzyme Q10 encapsulated in the coenzyme Q10 solubilizing composition was quantified through HPLC analysis.

Figure 15:
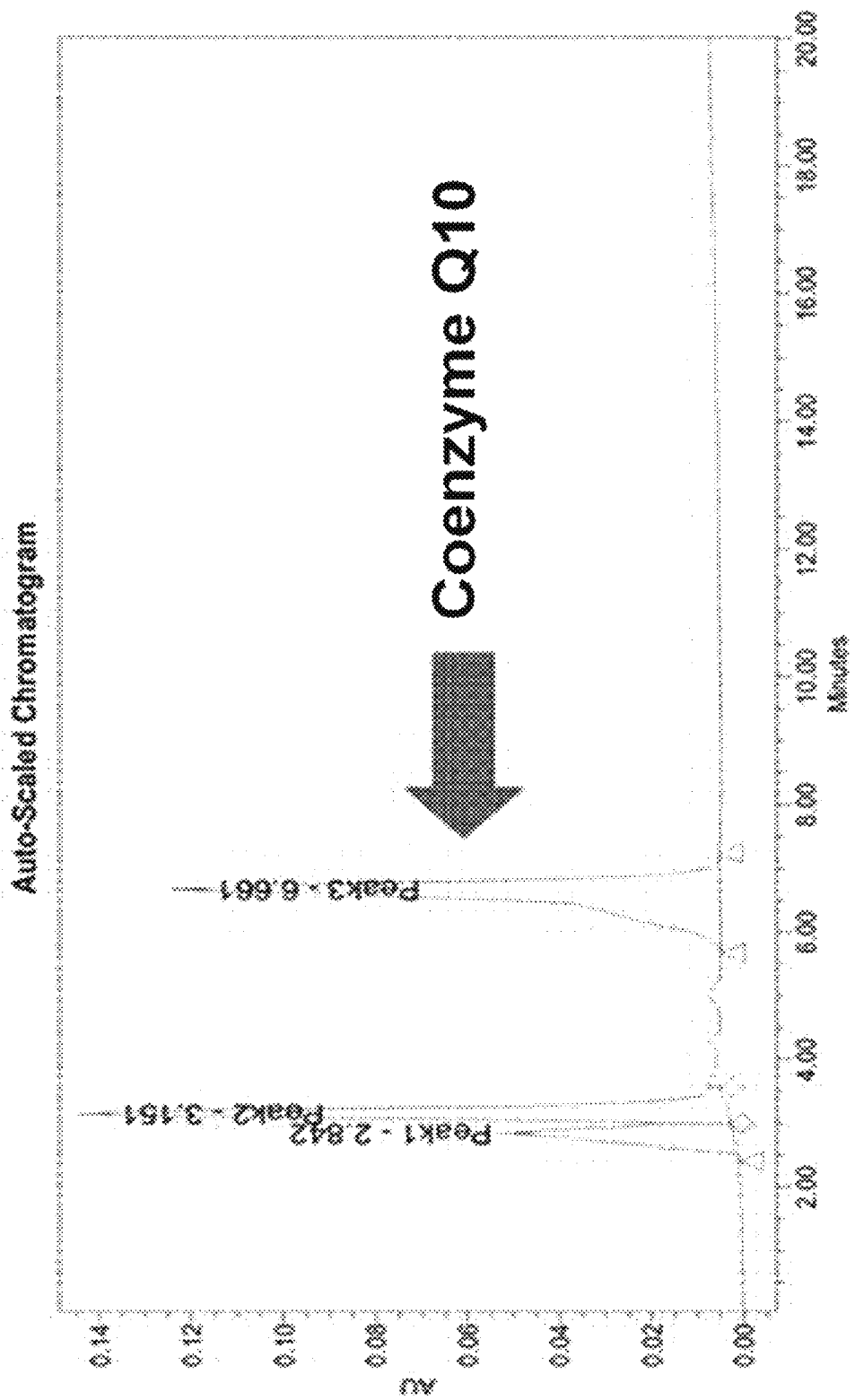
FIG. 15 is a quantitative graph showing analysis results of a coenzyme Q10 solubilizing composition prepared using a microfluidizer.

As a result, the degree of solubilization of coenzyme Q10 in the coenzyme Q10 solubilizing composition prepared using a microfluidizer was determined through the coenzyme Q10 graph as illustrated in FIG. 15 and by Equation 1 below.

More particularly, 0.185 mg of coenzyme Q10 was encapsulated in 1 mg of a micelle (HPLC UV=0.113 at 6.6 min), and since 6.2 g/L of a micelle was dissolved, the degree of solubilization of coenzyme Q10 per liter is as follows.

$$6,200 \text{ mg} \times 0.185 \text{ mg}/1,000 \text{ mL} = 1.15 \text{ mg/mL} \qquad [\text{Equation 1}]$$

4-5. Preparation of Coenzyme Q10 Solubilizing Composition Including Ascorbic Acid (Vitamin C)

Figure 11A:
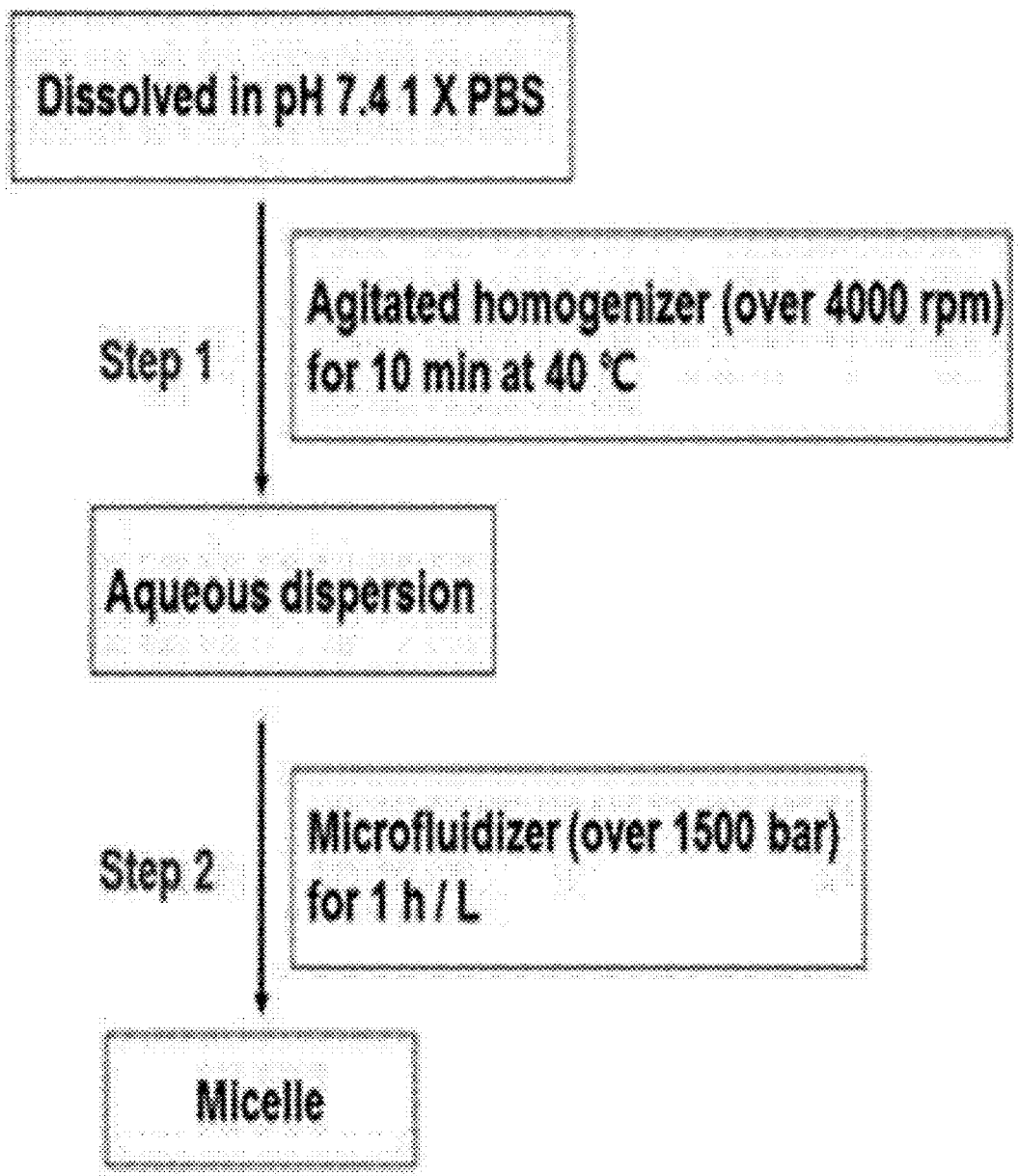
FIG. 11A illustrates a method of preparing an unsaturated coenzyme Q10 solubilizing composition.
Figure 11B:
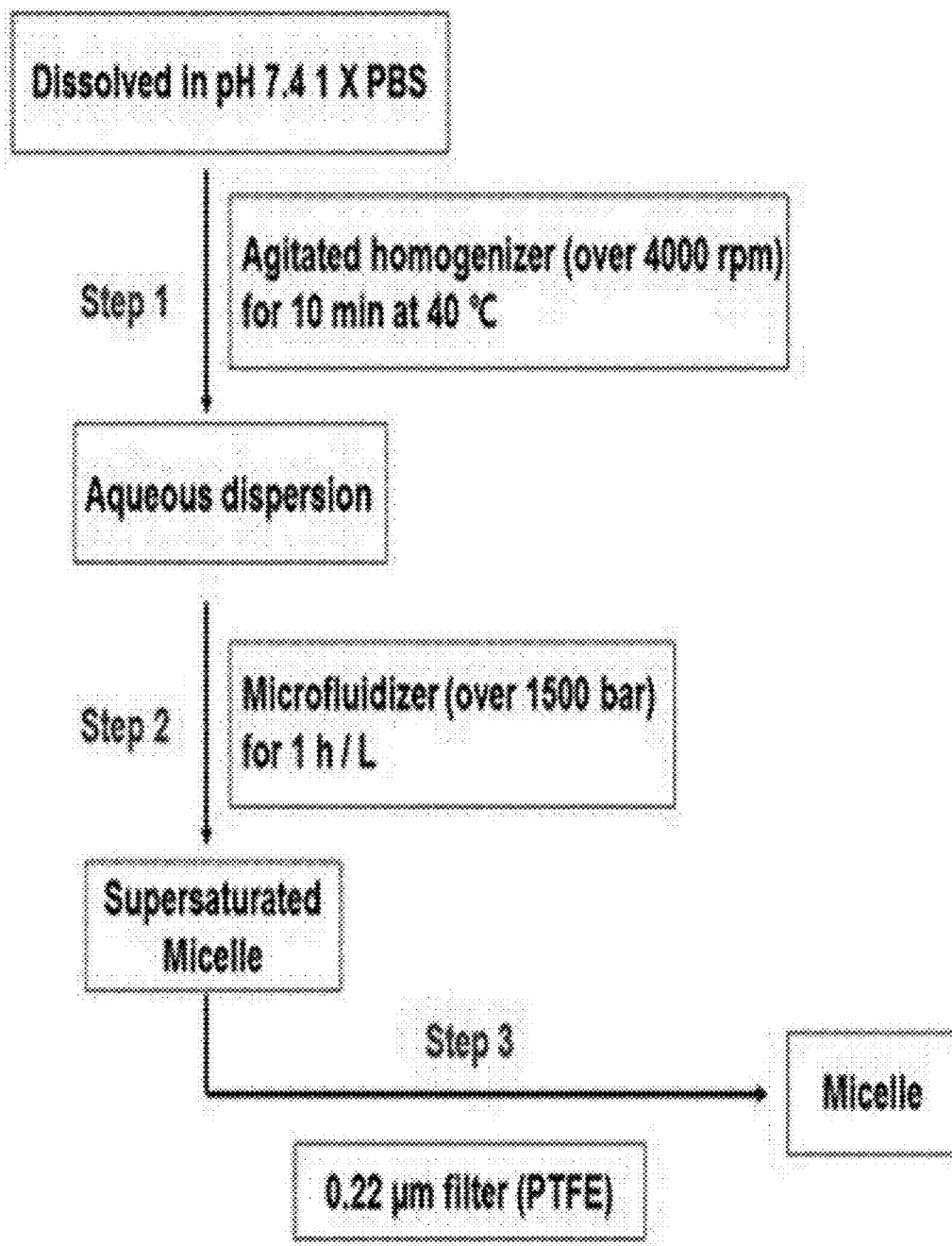
FIG. 11B illustrates a method of preparing a supersaturated coenzyme Q10 solubilizing composition.

A coenzyme Q10 solubilizing composition including ascorbic acid and a high concentration of coenzyme Q10 was prepared according to the preparation method illustrated in FIG. 11.

More particularly, distilled water was injected into a reactor, and then dipotassium glycyrrhizinate, eicosapentaenoic acid (EPA), ascorbic acid, and cholic acid for the formation of a micelle, and coenzyme Q10, which is a poorly water-soluble drug, were added in amounts of 3.6 g, 1.2 mL, 1.2 g, 0.6 g, and 1.2 g (6:2:2:1:2), respectively and stirred at 45° C. and 4,000 rpm for 10 minutes to a uniform dispersion. The reaction solution was used to perform the encapsulation of coenzyme Q10 through the formation of a micelle by using an APV-2000 microfluidizer manufactured by APV at a high pressure of 1,500 bars for 1 hour, and a micelle was obtained using a 0.22 µm syringe filter. At this time, in the case of the composition in a supersaturated state, coenzyme Q10 remaining not encapsulated in an aqueous solution after solubilizing the composition by using a microfluidizer was removed using a 0.22 µm syringe filter, and the filtrate was stored at 4° C. for 12 hours and subjected to filtration again using a 0.22 µm syringe filter, followed by storage at a low temperature of 4° C.

Figure 16:
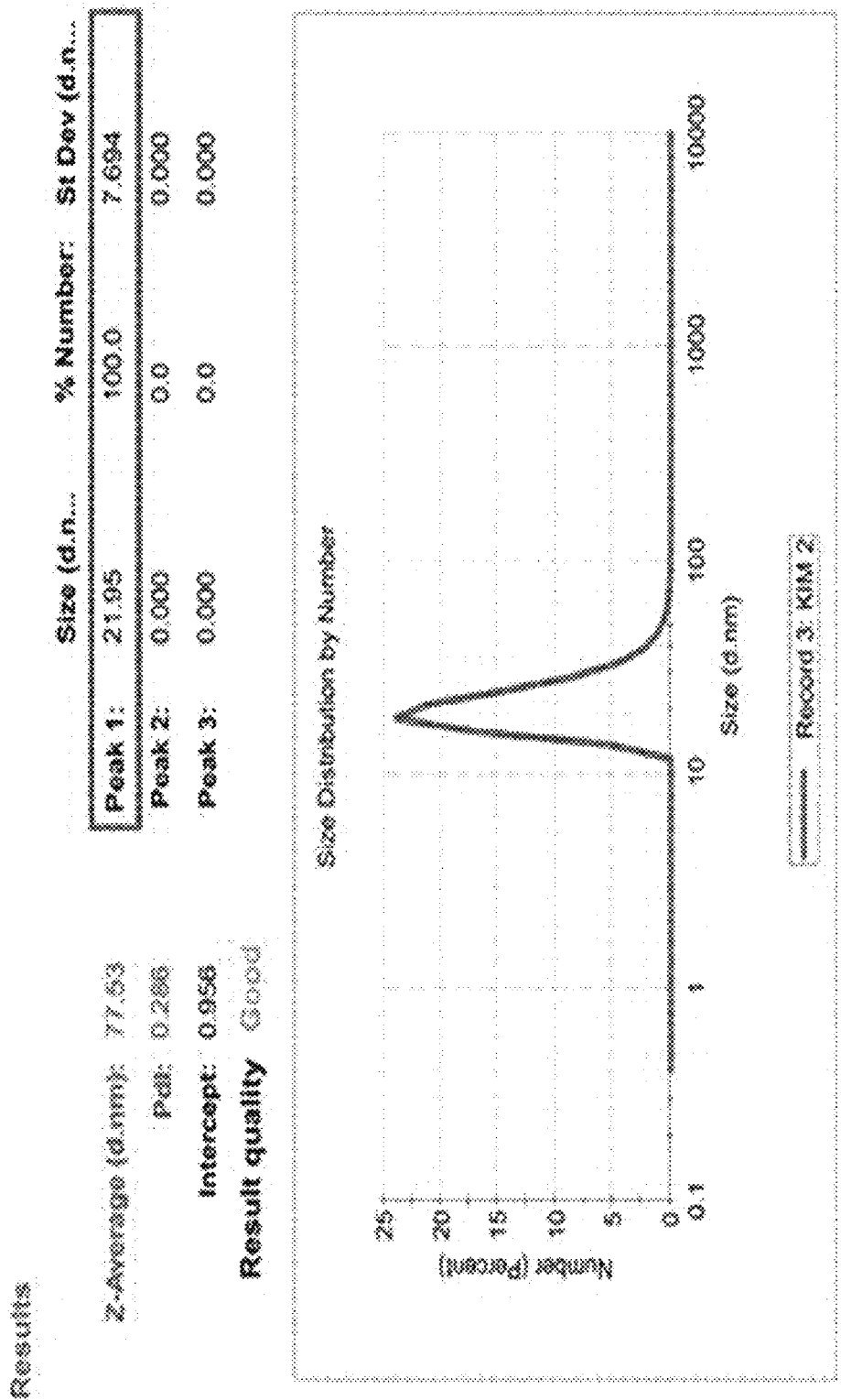
FIG. 16 illustrates particle size distribution analysis results of a coenzyme Q10 solubilizing composition including ascorbic acid, prepared using a microfluidizer.

At this time, as illustrated in FIG. 16, as a result of particle size analysis showing the particle size of a micelle of water-soluble coenzyme Q10 including ascorbic acid, it was confirmed that the coenzyme Q10 solubilizing composition had a uniform particle size of about 20 nm.

4-6. Quantification of Coenzyme Q10 Solubilizing Composition Including Ascorbic Acid (Vitamin C)

The quantification of coenzyme Q10 was performed in 6.4 g/L of the coenzyme Q10 solubilizing composition prepared by the method described in Example 4-1 above using glycyrrhizic acid, coenzyme Q10, eicosapentaenoic acid, ascorbic acid, cholic acid (3.6 g: 1.2 g: 1.2 mL: 1.2 g: 0.6 g), and 1 L of distilled water. At this time, the above-described conditions are optimum conditions in preparation of a coenzyme Q10 solubilizing composition in accordance with the ratio of glycyrrhizic acid:coenzyme Q10:eicosapentaenoic acid:ascorbic acid:cholic acid of 0.1 to 5:0.1 to 5:0.1 to 5:0.1 to 5:0.1 to 5, and a range in which the raw materials are mixed may be changed based on Example 2-1 above and Example 4-1 above.

More particularly, 1 mg of the coenzyme Q10 solubilizing composition prepared using the above method was dissolved in 1 mL of an alcohol to elute coenzyme Q10 therefrom, and then coenzyme Q10 encapsulated in the coenzyme Q10 solubilizing composition was quantified through HPLC analysis.

Figure 17:
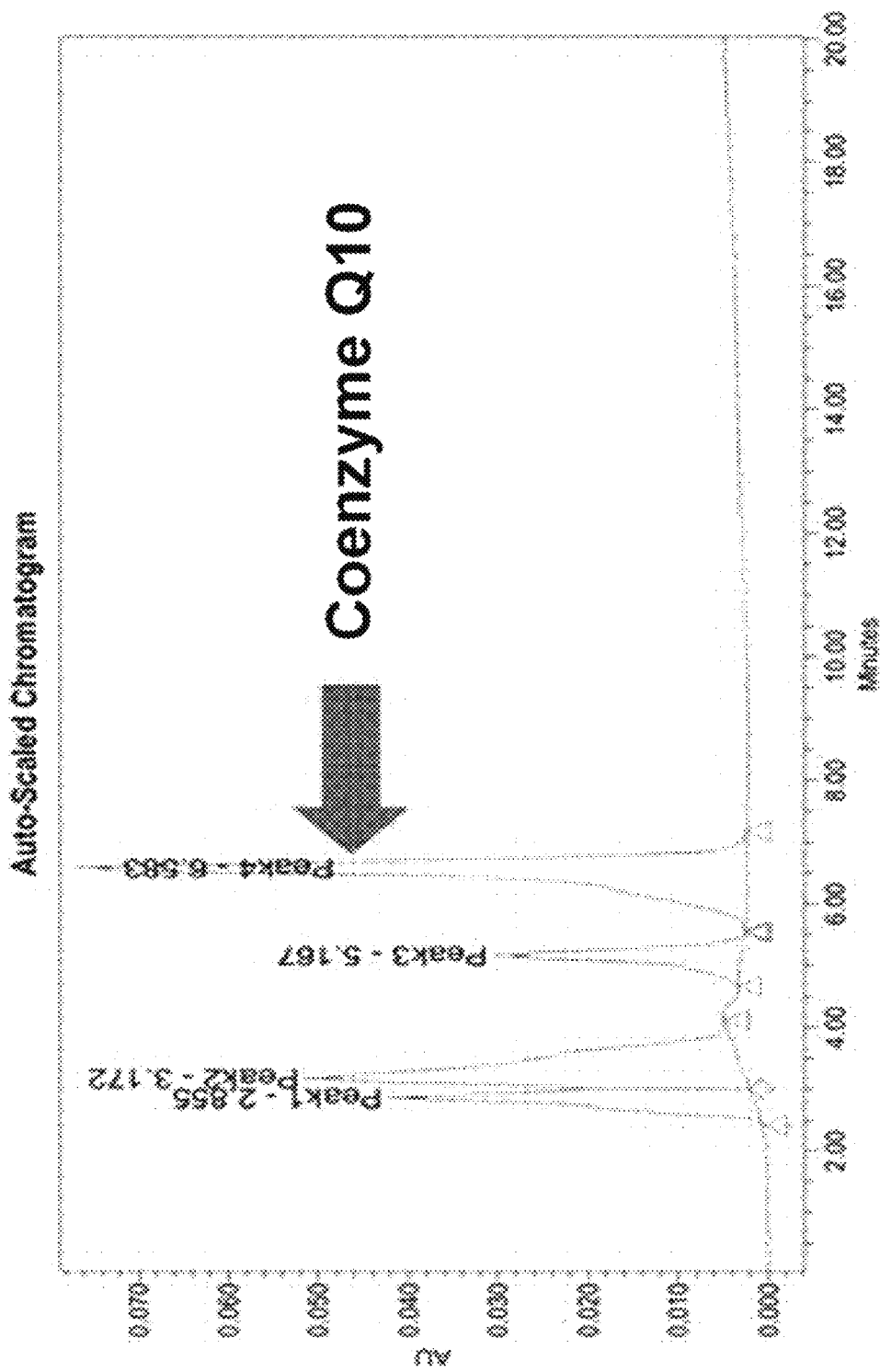
FIG. 17 is a quantitative graph showing analysis results of a coenzyme Q10 solubilizing composition including ascorbic acid, prepared using a microfluidizer.

As a result, the degree of solubilization of coenzyme Q10 in the coenzyme Q10 solubilizing composition prepared using a microfluidizer was determined through the coenzyme Q10 graph as illustrated in FIG. 17 and by Equation 2 below.

More particularly, 0.12 mg of coenzyme Q10 was encapsulated in 1 mg of a micelle (HPLC UV=0.0716 at 6.6 min), and since 6.4 g/L of a micelle were dissolved, the degree of solubilization of coenzyme Q10 per liter is as follows.

$$6,400 \text{ mg} \times 0.12 \text{ mg}/1,000 \text{ mL} = 0.77 \text{ mg/mL} \qquad [\text{Equation 2}]$$

4-7. Quantification of Ascorbic Acid (Vitamin C) of Coenzyme Q10 Solubilizing Composition The quantification of ascorbic acid was performed in 6.4 g/L of the coenzyme Q10 solubilizing composition prepared by the method described in Example 4-1 above using glycyrrhizic acid, coenzyme Q10, eicosapentaenoic acid, ascorbic acid, cholic acid (3.6 g: 1.2 g: 1.2 mL: 1.2 g: 0.6 g), and 1 L of distilled water.

More particularly, 1 mg of the coenzyme Q10 solubilizing composition including ascorbic acid was dissolved in 1 mL of an alcohol to elute ascorbic acid therefrom, and then ascorbic acid encapsulated in the coenzyme Q10 solubilizing composition was quantified through HPLC analysis. In this case, the HPLC analysis was performed using a Waters 2695 HPLC model manufactured by Waters, and for a column, Xbridge C18 (4.6×250 mm, 5 µm; Waters) was used, and for mobile-phase solvents, water including 0.075% trifluoroacetic acid was used as solvent A and acetonitrile including 0.1% trifluoroacetic acid was used as solvent B. Ascorbic acid was measured through absorbance at 250 nm, and a quantitative graph of ascorbic acid was plotted (see FIGS. 18 and 19).

TABLE 3

| Time | Solvent A: 0.075% TFA in Water | Solvent B: 0.1% TFA in ACN |
|---|---|---|
| 0 min to 5 min | 90% | 10% |
| 5 min to 10 min | 20% | 80% |
| 10 min to 15 min | 20% | 80% |
| 15 min to 16 min | 90% | 10% |
| 16 min to 20 min | 90% | 10% |

Figure 18:
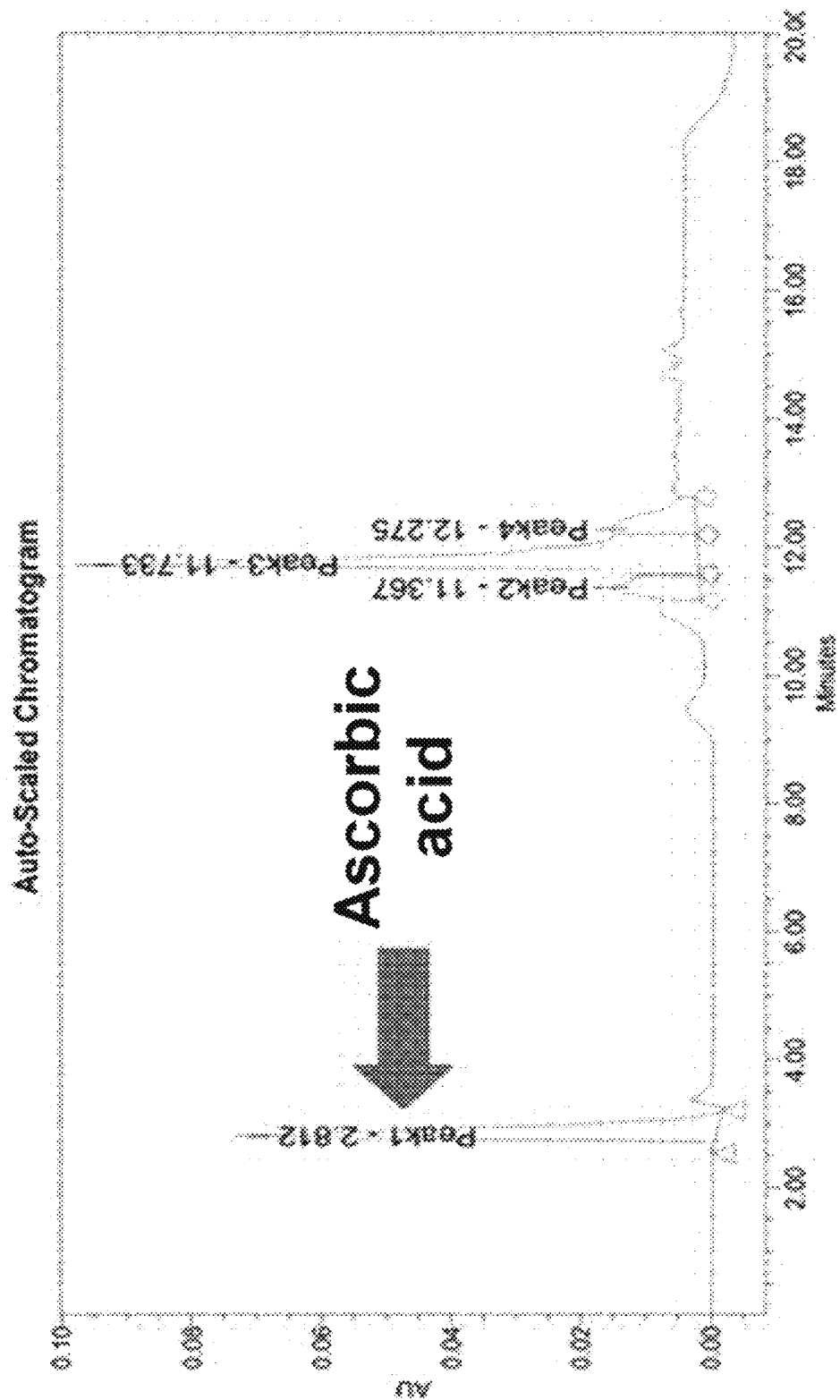
FIG. 18 illustrates results of analyzing a graph for quantifying ascorbic acid in a coenzyme Q10 solubilizing composition including ascorbic acid, prepared using a microfluidizer.
Figure 19:
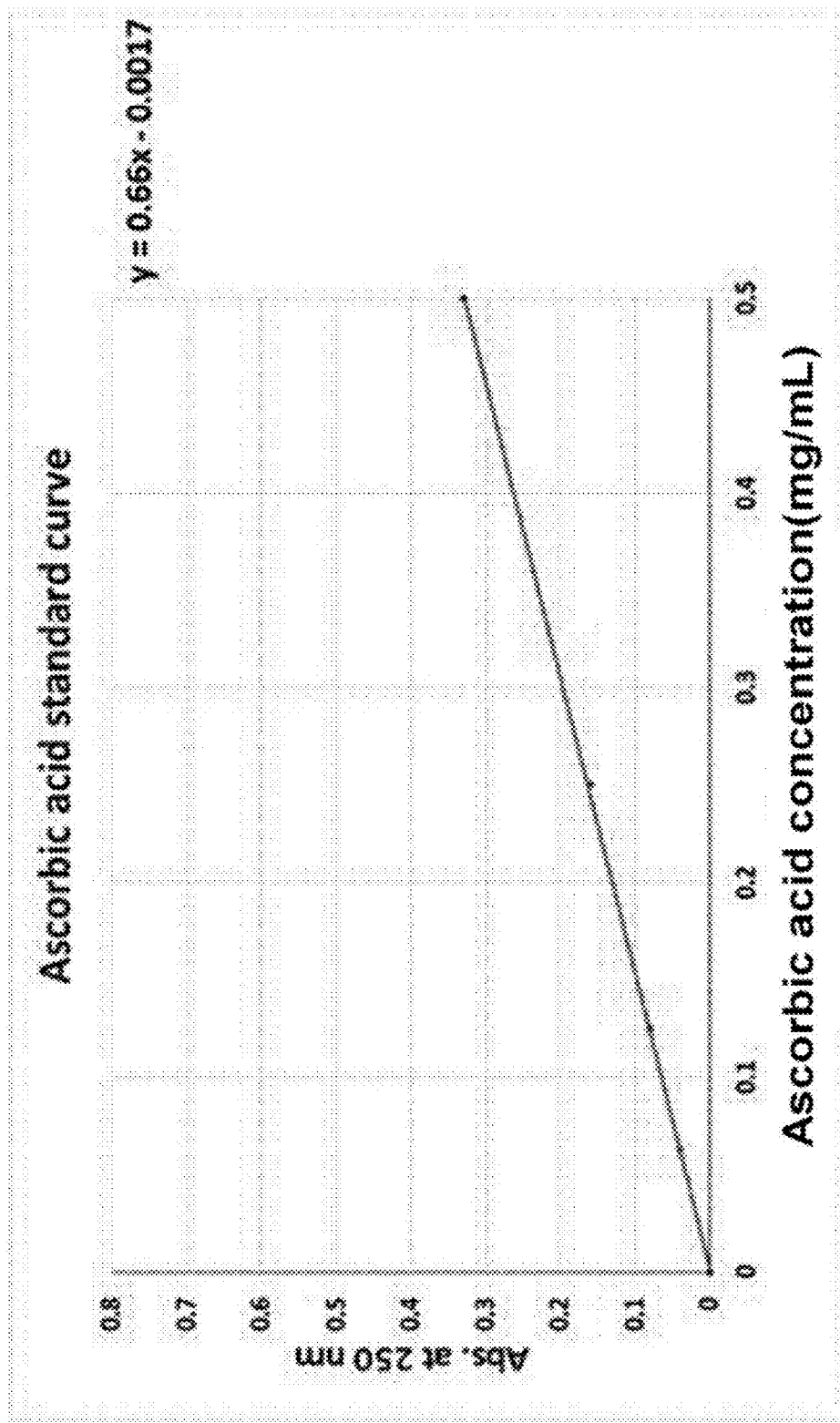
FIG. 19 is a quantitative curve showing HPLC analysis results of ascorbic acid at various concentrations.

As a result, as illustrated in FIG. 18, ascorbic acid showing an absorbance of 0.07 at an absorption wavelength of 250 nm was identified at 2.8 minutes in the water-soluble coenzyme Q10 solubilizing composition. In this case, the degree of solubilization of ascorbic acid in the coenzyme Q10 solubilizing composition prepared using a microfluidizer was determined by Equation 3 below.

More particularly, 0.11 mg of ascorbic acid was encapsulated in 1 mg of a micelle of coenzyme Q10 (HPLC UV=0.07 at 2.8 min), and since 6.4 g/L of a micelle were dissolved, the degree of solubilization of ascorbic acid per liter is as follows.

$$6,400 \text{ mg} \times 0.11 \text{ mg}/1,000 \text{ mL} = 0.7 \text{ mg/mL} \qquad [\text{Equation 3}]$$

The foregoing description of the present invention is provided for illustrative purposes, and it will be understood by those of ordinary skill in the art to which the present invention pertains that the invention may be easily modified in many different forms without departing from the technical spirit or essential characteristics of the present invention. Therefore, it is to be understood that the above-described embodiments are illustrative and not restrictive in all aspects.

INDUSTRIAL APPLICABILITY

According to the present invention, coenzyme Q10 and/or an unsaturated fatty acid, which are/is known to have low bioavailability due to low water solubility and poor absorption in the gastrointestinal tract while having various physiological activities such as anti-inflammatory activity, and the like, are/is solubilized to thereby enhance pharmacokinetic (PK) properties, and pharmaceutical application of the composition in the corresponding field is anticipated.

The invention claimed is:

1. A coenzyme Q10 solubilizing composition in which coenzyme Q10 is encapsulated in a micelle comprising glycyrrhizic acid or a salt thereof, a bile acid or a salt thereof, and an unsaturated fatty acid;
   wherein the unsaturated fatty acid is eicosapentaenoic acid (EPA) or docosahexaenoic acid (DHA) and wherein the coenzyme Q10 solubilizing composition is cyclodextrin-free.

2. The coenzyme Q10 solubilizing composition of claim 1, wherein the coenzyme Q10 solubilizing composition further comprises ascorbic acid.

3. The coenzyme Q10 solubilizing composition of claim 1, wherein the bile acid comprises any one or more selected from the group consisting of cholic acid, deoxycholic acid, and ursodeoxycholic acid.

4. The coenzyme Q10 solubilizing composition of claim 1, wherein an amount of the encapsulated coenzyme Q10 in the coenzyme Q10 solubilizing composition ranges from 1 wt % to 50 wt % with respect to a total weight of the composition.

5. The coenzyme Q10 solubilizing composition of claim 1, wherein the coenzyme Q10 is included at a concentration of 0.05 mg/mL to 3 mg/mL in an aqueous coenzyme Q10 solubilizing composition solution.

6. The coenzyme Q10 solubilizing composition of claim 1, wherein a mixing ratio of the glycyrrhizic acid or a salt thereof, the bile acid or a salt thereof, the unsaturated fatty acid, and the coenzyme Q10 is 0.1 to 5:0.1 to 5:0.1 to 5:0.1 to 5 on a weight basis.

7. The coenzyme Q10 solubilizing composition of claim 1, wherein the coenzyme Q10 solubilizing composition has a particle size of 10 nm to 200 nm.

8. The coenzyme Q10 solubilizing composition of claim 1, wherein the composition comprises a pharmaceutical composition.

9. The coenzyme Q10 solubilizing composition of claim 1, wherein the composition comprises a food composition.

10. The coenzyme Q10 solubilizing composition of claim 1, wherein the composition comprises a cosmetic composition.

11. A method of preparing a coenzyme Q10 solubilizing composition, the method comprising:
    (1) preparing a suspension by adding glycyrrhizic acid or a salt thereof, a bile acid or a salt thereof, an unsaturated fatty acid, and coenzyme Q10 to a solvent and then performing stirring; and
    (2) homogenizing the suspension by sonication or using a microfluidizer;
    wherein the unsaturated fatty acid is eicosapentaenoic acid (EPA) or docosahexaenoic acid (DHA).

12. The method of claim 11, further comprising: (3) purifying the coenzyme Q10 solubilizing composition prepared by the homogenization (process (2)), through a filter.

13. The method of claim 12, further comprising: (4) purifying the coenzyme Q10 solubilizing composition, which is present in a form of a filtrate obtained by the purification (process (3)), through a filter after storage at 0° C. to 4° C.

14. The method of claim 11, wherein the suspension further comprises ascorbic acid.

* * * * *